United States Patent [19]
Danishefsky et al.

[11] Patent Number: 5,113,014
[45] Date of Patent: May 12, 1992

[54] PROCESSES FOR PREPARING PROSTAGLANDINS

[75] Inventors: Samuel J. Danishefsky; Ken H. Chow; Carmen M. P. C. Naves, all of New Haven, Conn.

[73] Assignee: Yale University, New Haven, Conn.

[21] Appl. No.: 450,099

[22] Filed: Dec. 13, 1989

[51] Int. Cl.⁵ .......................................... C07C 177/00
[52] U.S. Cl. .................................... 562/503; 560/121
[58] Field of Search .................... 560/121; 562/503

[56] References Cited

PUBLICATIONS

Journal of the American Chemical Society Nov. 29, 1972; Efficient Generation of the 15S Configuration in Prostaglandin Synthesis. Attractive Interactions in Stereochemical Control of Carbonyl Reduction. pp. 8616-8618.
Journal of the American Chemical Society 1988; pp. 4718-4726; The Three-Component Coupling Synthesis of Prostaglandins. M. Suzuki, et al vol. 110.
Journal of the American Chemical Society, 1988, vol. 110; pp. 4726-4735 Triply Convergent Synthesis of (−)-Prostaglandin E₂ Methyl Ester; Carl R. Johnson et al.
Communications to the Editor; pp. 4745-4746; A General Approach to Prostaglandins via Methylenecyclopentanones. Total Synthesis of (±)-Prostaglandin F₂α (1975).
Communications to the Editor pp. 5843-5844; (1979).
Tetrahedron Letters, vol. 23, No. 39 pp. 4057-4060, 1982; A Facile Synthesis of (−)-Prostaglandin E₁ Via a Three-Component Coupling Process M. Suzuki et al.
Tetrahedron Letters, vol. 27, No. 20, pp. 2199-2202, 1986; A New Synthetic Route to Prostaglandins; E. J. Corey et al.
Tetrahedron Letters, vol. 28, No. 46, pp. 5655-5658, 1987; Synthesis of Novel Prostaglandin F₂ Isomers and structure of an enzymatically formed 13-Hydroxyprostaglandin Endoperoxide; Ute Hofmann et al.
Angew. Chemical Int. Ed. Engl. 22 1983; pp. 803-815; From Studies of Biochemical Mechanism to Novel Biological Mediators: Prostaglandin Endoperoxides Thromboxanes, and Leukotrienes (Nobel Lecture).
Danishefsky et al., I JACS 111, 3456 (1989).
Danishefsky et al., II JOC 54 6016 (1989).
Danishefsky et al. JACS 111 2599 (1989).

*Primary Examiner*—Robert Gerstl
*Attorney, Agent, or Firm*—Sprung, Horn, Kramer & Woods

[57] ABSTRACT

A process for the preparation of a prostaglandin of the formula

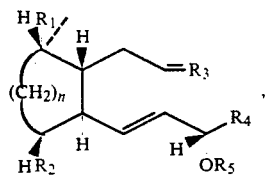

wherein n is 1, 2, 3 or 4,
$R_1$ and $R_2$, independently of each other, are alkyl, OH, alkoxy, ketone, halogen, hydrogen, nitro, amino or ether,
$R_3$ is hydrogen, alkyl, haloalkyl or carboxyalkyl,
$R_4$ is hydrogen, alkyl or haloalkyl,
$R_5$ is hydrogen, alkyl or haloalkyl comprising (a) reacting an S-enone of the formula

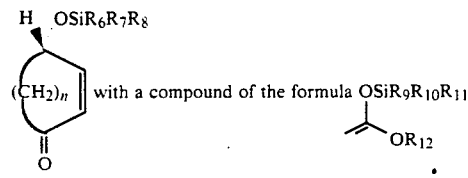

in the presence of a Lewis acid, wherein n is 1, 2, 3 or 4,
$R_6$, $R_7$ and $R_8$ are alkyl or any two or three combined are cycloalkyl or aryl,
$R_9$, $R_{10}$ and $R_{11}$ are alkyl or any two or three combined are cycloalkyl or aryl,
$R_{12}$ is hydrogen or alkyl
(b) reacting the compound from (a) with an aldehyde in the presence of $TiCl_4$,
(c) acetylating the compound from (b),
(d) reacting the compound from (c) with $Pd(MeCN)_2Cl_2$,
(e) reducing the compound from (d),
(f) acetylating the compound from (e),
(g) reacting the compound from (f) with TBAF,
(h) reacting the compound from (g) with DIBAH and
(i) reacting the compound from (h) with a Wittig reagent.

35 Claims, No Drawings

PROCESSES FOR PREPARING PROSTAGLANDINS

GOVERNMENT RIGHTS

This invention was made with United States government support under PHS Grant HL 25848. The United State government has certain rights in this invention.

BACKGROUND OF THE INVENTION

1. Field of the Invention

The present invention concerns processes to produce prostaglandins.

2. Background Information

There are few substances that currently command more widespread interest in biological circles than do the prostaglandins and the related products of arachidonic acid metabolism. Although their history extends back to the early 1930s, it was the isolation, characterization, and synthesis of the representative compounds in the early 1960s that generated such intense interest. The reasons are not hard to find. The prostaglandins are among the most prevalent of autacoids and have been detected in almost every tissue and body fluid; their production increases in response to astonishingly diverse stimuli; they produce, in minute amounts, a remarkably broad spectrum of effects that embraces practically every biological function; and inhibition of their biosynthesis is now recognized as a mechanism of some of the most widely used therapeutic agents, the nonsteroidal anti-inflammatory drugs such as aspirin.

A harbinger of this remarkable development was the observation made in 1930 by two American gynecologists, Kurzrok and Lieb, that strips of human uterus relax or contract when exposed to human semen. A few years later, Goldblatt in England and Euler in Sweden independently reported smooth-muscle-contracting and vasodepressor activity in seminal fluid and accessory reproductive glands, and Euler identified the active material as a lipid-soluble acid, which he named "prostaglandin". More than 20 years were to pass before technical advances allowed the demonstration that prostaglandin was in fact a family of compounds of unique structure, permitted the isolation in crystalline form of two prostaglandins, prostaglandin $E_1$ ($PGE_1$) and $PGF_{1\alpha}$, and led to the elucidation of their structures in 1962. Soon, more prostaglandins were characterized and, like the others, proved to be 20-carbon unsaturated carboxylic acids with a cyclopentane ring.

When the general structure of the prostaglandins became apparent, their kinship with essential fatty acids was recognized, and in 1964 Bergström and coworkers and van Dorp and associates independently achieved the biosynthesis of $PGE_2$ from arachidonic acid using homogenates of sheep seminal vesicle.

Until recently it was believed that $PGE_2$ and $PGF_{2\alpha}$ were the most important prostaglandins. Indeed, thousands of analogs of these compounds were made in the largely frustrated hope that compounds of therapeutic value with a greater selectivity of action would emerge. However, since 1973, several discoveries have caused a radical shift in emphasis away from PGEs and PGFs. The first was the isolation and identification of two unstable cyclic endoperoxides, prostaglandin $G_2$ ($PGG_2$ or 15-OOH $PGH_2$) and prostaglandin $H_2$ ($PGH_2$). Later came the elucidation of the structure of thromboxane $A_2$ ($TXA_2$) and that of its degradation product, thromboxane $B_2$ ($TXB_2$) and then the discovery of prostacyclin ($PGI_2$). These findings, coupled with the elucidation of a different enzymatic pathway (a lipoxygenase), which converts arachidonic acid to compounds such as 12-hydroperoxyeicosatertraenoic acid (HPETE) and 12-hydroxyeicosatetraenoic acid (HETE), have led to the realization that the "classically known" prostaglandins constitute only a fraction of the physiologically active products of arachidonic acid metabolism.

The notion of synthesizing prostaglandins by dialkylation of an $\alpha,\beta$-unsaturated ketone goes back to the early days of the field. For comprehensive reviews of prostanoid syntheses, see: (a) Bindra, J. S.; Bindra, R., *Prostaglandin Synthesis;* Academic Press: New York, 1977; (b) Mitra, A., *Synthesis of Prostaglandins;* Wiley-Interscience: New York, 1977; (c) Garcia, G. A.; Maldonado, L. A.; Crabbe, P., *Prostaglandin Research;* Crabbe, P., Ed.; Academic Press: New York, 1977; Chapter 6; (d) *New Synthetic Routes to Prostaglandins and Thromboxanes;* Roberts, S. M., Scheinmann, F., Eds.; Academic Press: London, 1982.

The first success in a fully functionalized setting was realized by Stork, G. and Isobe, M., *J. Am. Chem. Soc.,* 1975, 97, 4745. Major advances in conciseness and efficiency have been introduced by Noyori et al (Suzuki, M., Kawagishi, T.; Suzuki, I.; Noyori, R., *Tetrahedron Lett.;* 1982, 23, 4057 and Suzuki, M.; Yanagisawa, A.; Noyori, R., *J. Am. Chem. Soc.,* 1988, 110, 4718); Johnson et al (Johnson, C. R.; Penning, T. D., *J. Am. Chem. Soc.,* 1988, 110, 4726) and Corey et al (Corey, E. J.; Niimura, K.; Konishi, Y.; Hashimoto, S.; Hamada, Y., *Tetrahedron Lett.,* 1986, 27, 2199).

While there have been countless variations, a common theme is apparent. Addition of a nucleophilic version of the $C_{13}$-$C_{20}$ ("lower-chain") to $C_{12}$ generates a $C_8$-$C_9$ enolate which is trapped with an electrophile suitable for construction of the $C_7$-$C_1$ ("upper") chain. In these schemes, the R enatiomer is employed. The stereochemical rationale of this method is that the organometallic nucleophile (Nu) attacks anti to the OP group and the electrophile attacks $C_8$ anti to the "lower" chain installed at $C_{12}$. The proper configuration at $C_{15}$ is achieved either from the use of a suitable educt or by reduction of the $C_{15}$ ketone (Noyori, R.; Tomino, I.; Nishizawa, M., *J. Am. Chem. Soc.,* 1979, 101, 5843; Corey, E. J.; Becker, K. B.; Varma, R. K., *J. Am. Chem. Soc.,* 1972, 94, 8616).

The general outlines of the previous three-component strategy are implied in the following Scheme I, where $PGF_{2\alpha}$ is the goal system.

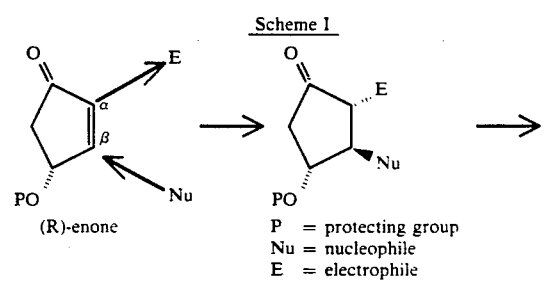

Scheme I

P = protecting group
Nu = nucleophile
E = electrophile

-continued
Scheme 1

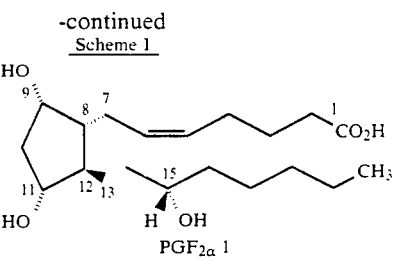

PGF$_{2\alpha}$ 1

There has also been interest in preparing prostaglandins that were heretofore produced by enzymatic conversion of arachidonic acid (Hoffmann, V., Meese, C. O., Hecker, M. and Volker, V., *Tetrahedron Lett.*, 1987, 28, 5655-5658; Hecker, M., Ullrich, V., Fischer, C. and Meese, C. O., *Eur. J. Biochem.*, 1987, 109 113-123).

The principal 9α,11α-endoperoxides arising from the in vivo oxidation of arachidonate in the presence of PGH synthase, contain a trans 13,14-double bond and either 15 S-hydroperoxy (PGG$_2$) or 15S hydroxy (PGH$_2$) functions (Samuelson, B., *Angew Chem. Int. Ed. Engl.*, 22, 805, 1983 and Hecker, M., Hatzelmann, A., Ullrich, V., Biochem. Pharmacol., 36, 851 (1987)). Surprisingly, it was recently shown that this process also produces allylic (14) isomers of the above, bearing oxygen substitution at C$_{13}$. Reduction of this endoperoxide gives rise to an allylic isomer of PGF$_{2\alpha}$ (Hecker, M., Hatzelmann, A., Ullrich, V., *Biochem. Pharmacol.*, 36, 851 (1987); Hecker, M., Ullrich, V., Fischer, C. and Meese, O. C., *Eur. J. Biochem.*, 113, 1987). That this prostaglandin is properly represented by structure 1' was demonstrated by Hoffman et al, supra. It would be advantageous to render the difficultly accessible naturally derived structure 1' and similar compounds available through total synthesis.

Scheme I' herein below depicts a typical enzymatic conversion of arachidonate with PGH synthase.

Scheme I' arachidonate $\xrightarrow{\text{PGH synthase}}$

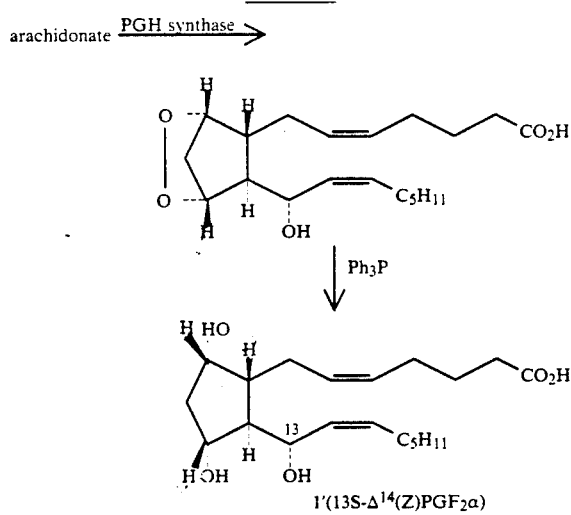

1'(13S-Δ$^{14}$(Z)PGF$_{2\alpha}$)

SUMMARY OF THE INVENTION

It is an object of the present invention to provide processes for the production of prostaglandins.

It is another object of the present invention to provide novel prostaglandins.

The above objects and other objects, aims, goals and advantages are satisfied by the present invention.

The present invention concerns a process ("Z-enal process") for the preparation of a prostagladin of the formula

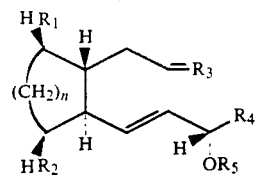

wherein n is 1, 2, 3 or 4,

R$_1$ and R$_2$, independently of each other, are alkyl having 1 to 10 carbon atoms, OH, alkoxy having 1 to 10 carbon atoms, a ketone having 2 to 10 carbon atoms, a halogen, hydrogen, nitro, an amino or an ether having up to 10 carbon atoms, R$_3$ is hydrogen, alkyl having 1 to 10 carbon atoms, haloalkyl having 1 to 10 carbon atoms or carboxyalkyl having 1 to 10 carbon atoms, R$_4$ is hydrogen, alkyl having 1 to 10 carbon atoms or haloalkyl having 1 to 10 carbon atoms, R$_5$ is hydrogen, alkyl having 1 to 10 carbon atoms or haloalkyl having 1 to 10 carbon atoms, comprising (a) reacting an S-enone of the formula

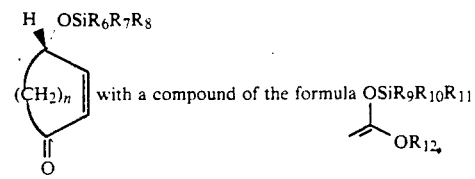

in the presence of a Lewis acid, wherein n is 1, 2, 3 or 4,

R$_6$, R$_7$ and R$_8$ combined having up to 16 carbon atoms. R$_6$, R$_7$ and R$_8$, independently of each other are alkyl having 1 to 6 carbon atoms or wherein a combination of any two or three of R$_6$, R$_7$ and R$_8$ form an aryl having 6 to 10 carbon atoms or a cycloalkyl having 3 to 10 carbon atoms, R$_9$, R$_{10}$ and R$_{11}$ combined having up to 16 carbon atoms, R$_9$, R$_{10}$ and R$_{11}$, independently of each other, are alkyl having 1 to 6 carbon atoms or wherein a combination of any two or three of R$_9$, R$_{10}$ and R$_{11}$ form an aryl having 6 to 10 carbon atoms or a cycloalkyl having 3 to 10 carbon atoms, R$_{12}$ is hydrogen or an alkyl having 1 to 10 carbon atoms, (b) reacting the compound produced from (a) with an α, β-unsaturated aldehyde of the formula

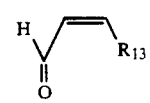

wherein R$_{13}$ is an alkyl having 1 to 10 carbon atoms or an aryl having 6 to 10 carbon atoms, in the presence of TiCl$_4$, (c) acetylating the compound produced from (b), (d) subjecting the compound produced from (c) to allylic transposition of the acetate with the formation of an $E_{13,14}$ double bond by, for example, reaction with $Pd(MeCN)_2Cl_2$, (e) reducing the compound produced from (d), by, for example, employing sodium borohydride, (f) acetylating the compound produced from (e), (g) subjecting the compound produced from (f) to a cleaving of $OSiR_6R_7R_8$ and a lactonizing, for example, with tetra-n-butyl ammonium fluoride (TBAF), (h) subjecting the compound produced from (g) to a deacylation, for example, with DIBAH and (i) reacting the compound produced from (h) with a Wittig reagent.

The present invention also relates to another process ("E-enal process") for the preparation of a prostagladin of the formula

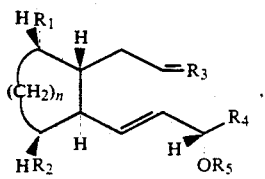

wherein n is 1, 2, 3 or 4, $R_1$ and $R_2$, independently of each other, are alkyl having 1 to 10 carbon atoms, OH, alkoxy having 1 to 10 carbon atoms, a ketone having 2 to 10 carbon atoms, a halogen, hydrogen, nitro, an amino or an ether having up to 10 carbon atoms, $R_3$ is hydrogen, alkyl having 1 to 10 carbon atoms, haloalkyl having 1 to 10 carbon atoms or carboxyalkyl having 1 to 10 carbon atoms, $R_4$ is hydrogen, alkyl having 1 to 10 carbon atoms or haloalkyl having 1 to 10 carbon atoms, $R_5$ is hydrogen, alkyl having 1 to 10 carbon atoms or haloalkyl having 1 to 10 carbon atoms, comprising (a) reacting an S-enone of the formula

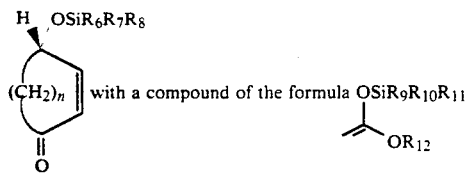

in the presence of a Lewis acid, wherein n is 1, 2, 3 or 4, $R_6$, $R_7$ and $R_8$ combined having up to 16 carbon atoms, $R_6$, $R_7$ and $R_8$, independently of each other, are alkyl having 1 to 6 carbon atoms or wherein a combination of any two or three of $R_6$, $R_7$ and $R_8$ form an aryl having 6 to 10 carbon atoms or a cycloalkyl having 3 to 10 carbon atoms, $R_9$, $R_{10}$ and $R_{11}$ combined having up to 16 carbon atoms, $R_9$, $R_{10}$ and $R_{11}$, independently of each other, are alkyl having 1 to 6 carbon atoms or wherein a combination of any two or three of $R_9$, $R_{10}$ and $R_{11}$ form an aryl having 6 to 10 carbon atoms or a cycloalkyl having 3 to 10 carbon atoms, $R_{12}$ is hydrogen or an alkyl having 1 to 10 carbon atoms, (b) reacting the compound produced from (a) with an α,β-unsaturated aldehyde of the formula

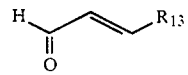

wherein $R_{13}$ is an alkyl having 1 to 10 carbon atoms or an aryl having 6 to 10 carbon atoms, in the presence of $TiCl_4$, (c) desilylating the compound produced from (b) with HOAc, THF and water (d) acetylating the compound produced from (c), (e) subjecting the compound produced from (d) to allylic transposition, by a reaction with, for example, $Pd(MeCN)_2Cl_2$, (f) reducing the compound produced from (e), (g) protecting the compound produced from (f), with a tetrahydropyranyl protecting group, e.g., para-methoxybenzyl or methoxymethyl, (h) subjecting the compound produced from (g) to desilylation and lactonization, e.g., with TBAF, (i) deacylating the compound produced from (h), employing, e.g., NaOMe, (j) subjecting the compound produced from (i) to a Mitsunobu reaction, (k) deacylating the compound produced from (j), for example, with diisobutyl aluminum hydride, (l) reacting the compound produced from (k) with a Wittig reagent and (m) reacting the compound produced from (l) with a weak organic acid, e.g., aqueous acetic acid, pyridinium P-toluenesulfonate or toluenesulfonic acid.

The present invention is further directed to a process (13-hydroxy prostaglandin process) for the preparation of a prostaglandin of the formula

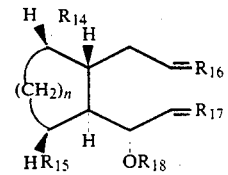

wherein n is 1, 2, 3 or 4, $R_{14}$ and $R_{15}$, independently of each other, are alkyl having 1 to 10 carbon atoms, OH, alkoxy having 1 to 10 carbon atoms, a ketone having 2 to 10 carbon atoms, a halogen, hydrogen, nitro, an amino or an ether having up to 10 carbon atoms, $R_{16}$ is hydrogen, alkyl having 1 to 10 carbon atoms, haloalkyl having 1 to 10 carbon atoms or carboxyalkyl having 1 to 10 carbon atoms, $R_{17}$ is hydrogen, alkyl having 1 to 10 carbon atoms or haloalkyl having 1 to 10 carbon atoms, $R_{18}$ is hydrogen, alkyl having 1 to 10 carbon atoms or haloalkyl having 1 to 10 carbon atoms, comprising (a) reacting an S-enone of the formula

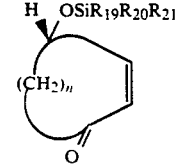

-continued with a compound of the formula $$\begin{array}{c} OSiR_{22}R_{23}R_{24} \\ | \\ OR_{12} \end{array}$$

in the presence of a Lewis acid, wherein n is 1, 2, 3 or 4, $R_{19}$, $R_{20}$ and $R_{21}$ combined having up to 16 carbon atoms, $R_{19}$, $R_{20}$ and $R_{21}$, independently of each other, are alkyl having 1 to 6 carbon atoms or wherein a combination of any two or three of $R_{19}$, $R_{20}$ and $R_{21}$ form an aryl having 6 to 10 carbon atoms or a cycloalkyl having 3 to 10 carbon atoms, $R_{22}$, $R_{23}$ and $R_{24}$ combined having up to 16 carbon atoms, $R_{22}$, $R_{23}$ and $R_{24}$, independently of each other, are alkyl having 1 to 6 carbon atoms or wherein a combination of any two or three of $R_{22}$, $R_{23}$ and $R_{24}$ form an aryl having 6 to 10 carbon atoms or a cycloalkyl having 3 to 10 carbon atoms, $R_{25}$ is hydrogen or an alkyl having 1 to 10 carbon atoms, (b) reacting the compound produced from (a) with a compound of the formula $$\begin{array}{c} H \\ \diagdown \\ \diagup \\ O \end{array} = R_{26}$$

in the presence of $TiCl_4$, wherein $R_{26}$ is an alkyl having 1 to 10 carbon atoms, (c) hydrogenating the compound produced from (b) with hydrogen and a hydrogenation catalyst, e.g., Lindlar's catalyst, (d) acetylating the compound produced from (c) with $AcO_2$, pyridine (Py) and 4-dimethylaminopyridine (DMAP), (e) reducing the compound produced from (d), (f) acetylating the compound produced from (e), (g) subjecting the compound produced from (f) to cleavage of $OSiR_{19}R_{20}R_{21}$ and a lactonization, for example, by reaction with TBAF and THF, (h) reductively deacetylating the compound produced from (g), and (i) reacting the compound produced from (h) with a Wittig reactant.

The present invention is also directed to prostaglandins of the formula wherein n, $R_{14}$, $R_{15}$, $R_{16}$, $R_{17}$ and $R_{18}$ are defined hereinabove, produced by the above described process. Such prostaglandins are not found in nature.

Still further the present invention relates to prostaglandins of the formula wherein n, $R_{14}$, $R_{15}$, $R_{16}$, $R_{17}$ and $R_{18}$ defined as above, such prostaglandins in amounts exceeding 10 mg, preferably in amounts exceeding 50mg and most preferably exceeding 1 gram.

Still further, the present invention involves a compound of the formula wherein n is 1, 2, 3 or 4, $R_{27}$, $R_{28}$ and $R_{29}$ combined having up to 16 carbon atoms, $R_{27}$, $R_{28}$ and $R_{29}$, independently of each other, are alkyl having 1 to 10 carbon atoms or wherein a combination of any two or three of $R_{27}$, $R_{28}$ and $R_{29}$ form an aryl having 6 to 10 carbon atoms or a cycloalkyl having 3 to 10 carbon atoms, $R_{30}$ is an alkyl having 1 to 10 carbon atoms, coalkyl having 1 to 10 carbon atoms, hydrogen or haloalkyl having 1 to 10 carbon atoms, $R_{31}$ is an alkyl having 1 to 10 carbon atoms or haloalkyl having 1 to 10 carbon atoms and, $R_{32}$ is hydrogen, alkyl having 1 to 10 carbon atoms or haloalkyl having 1 to 10 carbon atoms and wherein the halo portion is preferably fluorine, chlorine, iodine or bromine.

Such compound is useful as an intermediate in the production of prostagladins.

DETAILED DESCRIPTION OF THE INVENTION

In the above formulas, alkyl represents a straight-chain or a branched hydrocarbon radical. Non-limiting examples of alkyl are methyl, ethyl, propyl, isopropyl, butyl, isobutyl, pentyl, isopentyl, hexyl, isohexyl, heptyl, isoheptyl, octyl and isooctyl. The alkyl can be substituted, for example, by sulfur.

In the above formulas, cycloalkyl represents a cyclic hydrocarbon radical having 3 to 8 carbon atoms. Non-limiting examples of cycloalkyl are cyclopentyl, cyclohexyl, cycloheptyl and cyclooctyl. The term cycloalkyl also includes cycloalkyl alkyl, e.g., cyclopropylmethyl through cyclopropylbutyl or cyclohexylmethyl.

In the above formulas, alkoxy represents a straight-chain or branched hydrocarbon radical which has 1 to 12 carbon atoms and is bonded via an oxygen atom. Non-limiting examples of alkoxy are methoxy, ethoxy, propoxy, isopropoxy, butoxy, isobutoxy, pentoxy, isopentoxy, hexoxy, isohexoxy, heptoxy, isoheptoxy, octoxy or isooctoxy.

In the above formulas, aryl represents an aromatic radical having one to preferably two aromatic rings. Aryl can be substituted, for example, by a halogen, e.g., chlorine, fluorine, bromine or iodine, a $C_1$-$C_{12}$-alkyl, hydroxy, a $C_2$-$C_{12}$ alkene, amino, nitro or sulfur. Preferred aryl radicals are phenyl, naphthyl and biphenyl. Non-limiting examples of substituted aryl include phenoxy, tolyl, chlorophenyl, bromophenyl, fluorophenyl, nitrophenyl and phenylthio.

In the above formulas, halogen represents fluorine, chlorine, bromine or iodine, preferably fluorine, chlorine or bromine.

In the above formulas, the halogen part of halogenoalkyl comprises fluorine, chlorine, bromine or iodine and the alkyl part is a straight-chain or branched hydrocarbon.

In the above formulas, non-limiting examples of ethers are dimethyl ether, diethyl ether, diisopropyl ether and methyethylether.

In the above formulas, non-limiting examples of ketones are acetone, methylethylketone, acetophenone and benzophenone.

The ring structures of the six primary prostaglandins (A to F) are as follows:

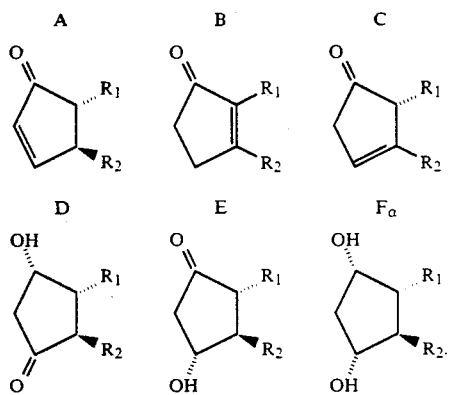

Non-limiting examples of Lewis acids for use in the present invention include $HgI_2$, $BF_3$, $SiF_4$, $SnCl_4$ and $AlCl_3$, with $HgI_2$ being preferred.

Wittig reactants for use in the processes of the invention have the formula

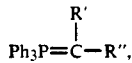

wherein R' and R", independently of each other are hydrogen, alkyl having 1 to 10 carbon atoms, carboxyalkyl having 1 to 10 carbon atoms, aryl having 6 to 10 carbon atoms and alkylaryl having 1 to 10 carbon atoms in the alkyl part and 6 to 10 carbon atoms in the aryl part, and salts thereof. Non-limiting examples of Wittig reactants include $Ph_3P$, $PH_3P=CH_2$, $C_6H_5CH=CH-CH=PPh_3$, $Ph_3P=CH-(CH_2)_3CO_2Na$ and $Ph_3P=CH-(CH_2)_3CO_2K$.

Non-limiting examples of hydrogenation catalysts for use in the present invention include Lindlar's catalyst (a palladium catalyst) and nickel borides.

One aspect of the present invention is a new process to synthesize prostaglandins of the type depicted in Scheme I as 1 ($PGF_{2\alpha}$), wherein the $C_{12}$-$C_{13}$ bond is established from an electrophilic version of $C_{13}$, and the $C_8$-$C_7$ bond is fashioned from a nucleophilic version of $C_7$. As will be seen, this method has significant advantages in terms of simplicity of building blocks and reactions. Either isomer at $C_{15}$ becomes readily available by stereochemical communication (Danishefsky, S. J., *Aldrichim. Acta*, 1986, 19, 59). The success of the route arises from the confluence of several rather interesting findings (as depicted in Schemes II to IV hereinabove which illustrate the invention with regard to specific compounds, but is not meant to limit the invention to such compounds). The first is that a group transfer reaction of (S)-enone 2 with the silylketeneacetyl derivative 3 occurs cis to the OTBS group to produce the specific enolate equivalent 4. This phenomenon which awaits full explanation is restricted to Lewis acid catalyzed additions (as opposed to cuprate additions which occur anti to the OTBS group). It has also been extended to $TiCl_4$ mediated addition of allyltrimethylsilane to 2. For similar results using 4-OTBS cyclohexenone, see: Danishefsky, S. J.; Simoneau, B., *Pure Appl. Chem.*, 1988, 60, 1555; Danishefsky, S. J.; Simoneau, B., *J. Am. Chem. Soc.*, 1989, 111,2599.

This enolate equivalent 4 reacts with (Z)-octenal (Byrne, B.; Lafleur-Lawter, L. M.; Wengenroth, K. J., *J. Org. Chem.*, 1986, 51, 2607) or E-octenal (5 and 6, respectively) (E-octenal is available from Aldrich Chemical Company) under catalysis by $TiCl_4$ to produce the $C_{12}$-$C_{13}$ syn aldol products (Mukaiyama, T.; Narasaka, K.; Banno, K., *Chem. Lett.*, 1973, 1011; Mukaiyama, T.; Banno, K.; Narasaka, K., *J. Am. Chem. Soc.*, 1974, 96, 7503; Masamune, S.; Ali, Sk. A.; Snitmann, D. C.; Garvey, D. S., *Angew. Chem. Int. Ed. Engl.*, 1980, 19, 557).

In each case, the aldehyde has entered trans to the carbethoxymethyl group and $C_8$. In each instance, the aldol process involves a second group transfer reaction of the triethylsilyl (TES or $SiEt_3$) unit. Each aldehyde attacks trans to the resident group at $C_8$, and a syn $C_{12}$-$C_{13}$ siloxyaldol system is produced in an essentially stereospecific reaction. In each instance selective cleavage of the TES function is achieved with maintenance of the OTBS group. A major complication arises if the TBS group is cleaved at this stage. With the $C_{11}$ ketone still in place, $\beta$-elimination occurs to give the enone.

For the product derived from 4+5 (Z-series), this selective desilylation is accomplished upon exposure of the system to the aldol reaction conditions ($TiCl_4$—$CH_2Cl_2$, $-85°$ C., 30 minutes). For the product derived from 4+6 (E-series), a subsequent reaction of the siloxy transfer product with aqueous AcOH-THF (tetrahydrofuran) achieves the same result. The resultant alcohols are acetylated ($Ac_2O$; Py; DMAP) to afford acetates 7 and 8 in the indicated yields.

The pathways from compound 7 and 8 to $PGF_{2\alpha}$ were very direct indeed. Reaction of compound 7 with $Pd(MeCN)_2Cl_2$ led to allylic transposition of the acetate with the formulation of the $E_{13,14}$ double bond and installation of the required 15S stereochemistry (see compound 9) in 72% yield.

For a most interesting precedent for this type of stereochemical adjustment in the [2,3] series, see: Miller, J. G.; Kurz, W.; Untch, K. G.; Stork, G., *J. Am. Chem. Soc.*, 1974, 96, 6774.

For the first application of the Pd(II)-mediated allylic acetate transposition to a modified prostaglandin intermediate, see: Grieco, P. A.; Takigawa, T.; Bongers, S. L.; Tanaka, H., *J. Am. Chem. Soc.*, 1980, 102, 7588.

Pd(II)-catalyzed allylic acetate transposition was first described by Meyer, K. DOS 2513198 (1975); *Chem. Abstr.*, 1976, 84, 89629s.

For a full review of Pd(II)-catalyzed [3,3] sigmatropic rearrangements, see: Overman, L. E., *Angew. Chem., Int. Ed. Engl.*, 1984, 23, 579.

At this stage (attempts to carry out the reduction of the $C_{11}$ ketone before the allylic transposition results, at best, in modest stereoselectivity possibly due to competing directivities from the 13-oxygen function) reduction of the $C_{11}$ ketone with sodium borohydride is stereospecific in the desired sense. Acetylation provided compound 11 in 74% yield (53% overall yield from 7). Cleavage of the TBS group and lactonization was accomplished through the action of TBAF. Reaction of 12 with DIBA (diisobutylaluminum hydride) resulted in formation of the lactol with deacylation to give compound 13 with in 72% overall yield from 11. Reaction of 13 with phosphorane 13' under the usual conditions gave, in 53% yield (Corey, E. J.; Winshenker, N. M.; Schaaf, T. K.; Huber, W., *J. Am. Chem. Soc.,* 1969, 91, 5675) $PGF_{2\alpha}$ (1) whose infrared and NMR spectra as well as optical rotation and chromatographic properties were identical with those of an authentic sample. The synthetic material had an optical rotation $[\alpha]_D +23.0°$ (c 1.01, THF) which is essentially the same as authentic $PGF_{2\alpha}$ ($[\alpha]_D +23.5°$, c 1.0, THF).

The same type of allylic transposition occurred even more rapidly with the E isomer 8. Not surprisingly the rate of transposition of the Z isomer is slower than that of the E isomer. For compound 7 conditions involved catalytic Pd(II) in THF at room temperature for 4 hours. For compound 8, the equivalent transformation was complete after 2 hours.

The rearrangement is unidirectional (compounds 9 and 15 failed to show indications of undergoing back rearrangement) and the $C_{13}$-$C_{14}$ double bond emerges cleanly trans. The stereochemistry at carbon 15 is of course R. Again, reduction of the $C_{11}$ ketone with sodium borohydride is stereospecific affording compound 16 which was protected as its tetrahydropyranyl ether 17 (69% overall yield from 8). Desilylation as above is accompanied by lactonization, and compound 18 is obtained in 84% yield. This substance is clearly a very valuable intermediate for preparing prostaglandins of the 15R series. It has been used to cross over to the natural series by inverting the stereochemistry at carbon 15. This was accomplished as follows. Deacylation of the 18 epiacetate afforded (98%) the 15R alcohol 19, which was inverted in a standard Mitsunobu reaction (a solution of 19 in THF was treated with triphenylphosphine (2 equiv.), benzoic acid (2 equiv) and diethylazodicarboxylate (2 equiv.) at room temperature; after 5 minutes the reaction was quenched with a solution of saturated $NaHCO_3$. See: (a) Mitsunobu. O.; Yamada, M., *Bull. Chem. Soc. Jpn.,* 1967, 40, 2380; (b) Mitsunobu, O., *Synthesis,* 1981, 1.) to the 15S benzoate 20 in 73% yield. Treatment of this compound with diisobutyl aluminum hydride resulted in reduction of the lactone and debenzoylation, affording compound 21. Reaction of this compound with Wittig reagent, 14, followed by cleavage of the THP protecting group (aqueous acetic acid), again afforded $PGF_{2\alpha}$ (1), this time in 46% yield from 20 (Corey et al, supra).

These routes offer major advantages in terms of conciseness, availability of all the building blocks, and simplicity of the reactions. Not the least advantage is the ready access to the required (S)-enone 2.

With respect to preparation of the starting material, see Scheme V hereinabove. The diacetate 22, available in multigram scale from cyclopentadiene (Deardorff, D. R.; Myles, D. C.; MacFerrin, K. D., *Tetrahedron Lett.,* 1985, 26, 5615), is converted through the action of acetylcholinesterase (Deardorff, D. R.; Matthews, A. J.; McMeekin, D. S.; Craney, C. L., *Tetrahedron Lett.,* 1986, 27, 1255) in 89% yield and, essentially total optical purity, to the monoacetate 23. Protection of the alcohol as its TBS derivative through the action TBSCl and imidazole in DMF affords 24 which on simple hydrolysis (sodium methoxide) leads to 25. The latter is oxidized with manganese dioxide to the optically pure (S)-enantiomer 2. The overall conversion of 22 to 2 is achieved in 70% yield.

The above described chemistry provides an eminently practical route for the total synthesis of prostaglandins and congeners thereof. The attraction of the inventive synthesis stems from the easy availability of all of its components and the ease of their assembly. In that vein, it is noted that to date the (S)-enone 2 is more readily obtained than is either the (R)-enone or, indeed, the racemate.

Scheme II

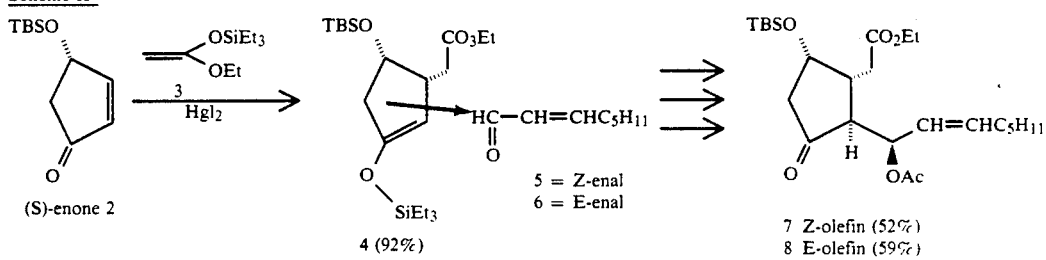

Scheme III
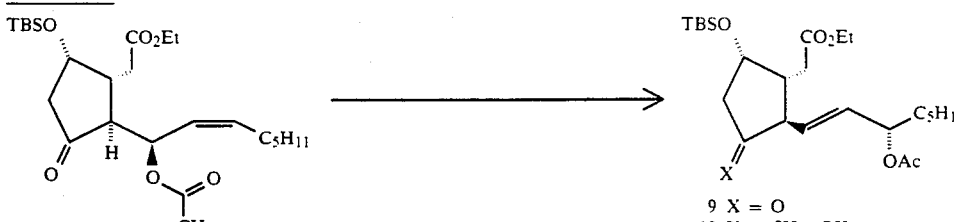
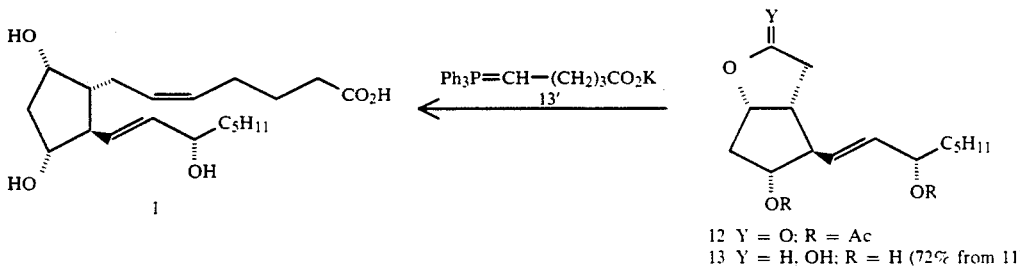
9 X = O
10 X = βH, αOH
11 X = βH, αOAc (53% from 7)
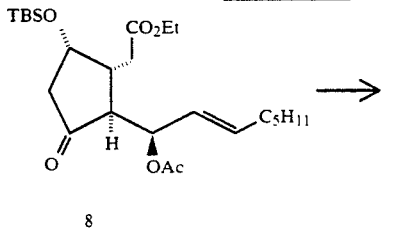
12 Y = O; R = Ac
13 Y = H, OH; R = H (72% from 11)
Scheme IV
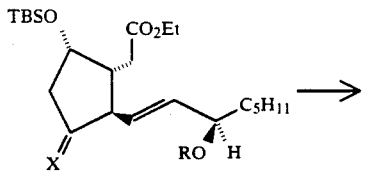
8
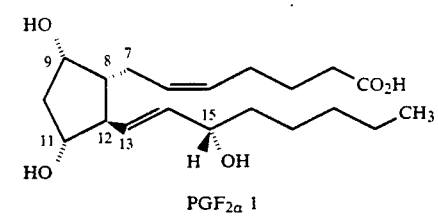
15 X = O; R = Ac
16 X = βH, αOH; R = Ac
17 X = βH, αOTHP; R = Ac
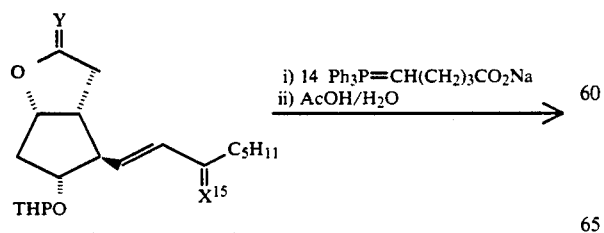
18 X = βOAc, αH; Y = O
19 X = βOH, αH; Y = O
20 X = αOBz, βH; Y = O
21 X = αOH, βH; Y = H, OH
-continued
Scheme IV
HO, 9, 8, 7, CO$_2$H, 11, 12, 13, 15, HO, H, OH, CH$_3$
PGF$_{2\alpha}$ 1
*THP = tetrahydropyranyl
Scheme V
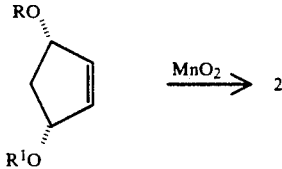
22 R = R$^1$ = Ac
23 R = H, R$^1$ = Ac
24 R = TBS, R$^1$ = Ac
25 R = TBS, R$^1$ = OH
Schemes II, III and IV are summarized as follows:

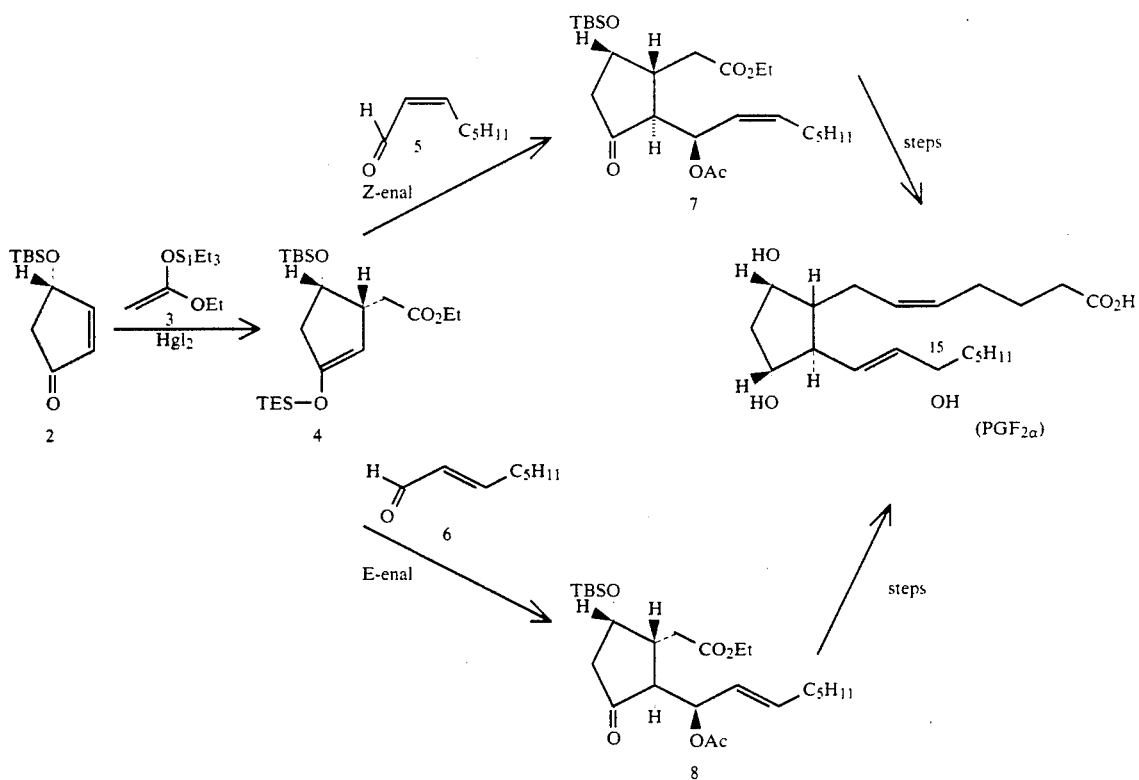

Another aspect of the present invention concerns a process to prepare prostaglandins such as 13 S- $^{14}(Z)$ PGF$_{2\alpha}$ (1'). As depicted in Scheme VI hereinbelow, which illustrates a process with specific compounds, but is not meant to limit the invention to such compounds, the key reaction is that of enoxysilane 4 with oct-2-ynal (7'). The reaction was carried out in methylene chloride in the presence of titanium tetrachloride (1 eq.) at $-75°$ C. for 15 minutes. There was thus obtained an acetylenic alcohol. Unlike the reactions with the two enals described hereinabove, the silyl group transfer product was not observed. At this stage, it was not possible to determine the stereochemistry at C$_{13}$.

Scheme VI shows semihydrogenation of the triple bond (H$_2$; Lindlar's catalyst, 50 minutes) afforded a Z-allylic alcohol which upon acetylation (Ac$_2$O, Py, DMAP, CH$_2$Cl$_2$), afforded a Z-allylic acetate in 50% overall yield from 2. This compound did not converge with any transformation products of 7. The non-correspondence arose from a differing configuration at C$_{13}$. The allylic acetate, thus formulated as 9', upon treatment with Pd(MeCN)$_2$Cl$_2$ afforded compound (11'=15). The same compound was obtained from an allylic transportation carried out in the same way on compound 8. The structure of 11' is secure in that it had been converted to PGF$_{2\alpha}$ by a sequence which involved inversion at C$_{15}$. Accordingly, the structures of compound 8' and 9' are as shown.

With the structure of allylic acetate 9' vouchsafed, the completion of the total synthesis of 1' was a straightforward matter. Reduction of cyclopentanone with sodium boroyhydride at 0° C. for 20 minutes followed by acetylation led to a 79% yield of 10'. Cleavage of the TBS group (TBAF, THF for 45 minutes) afforded lactone 12' in a yield of 89%. Reductive deacetylation was accomplished after exposure of 12'to DIBAH (5 eq; toluene; $-78°$ C. for 15 minutes). Reaction of this hemiacetal diol with readily available phosphorane 13' for 5 hours afforded 1' in 77% yield from 12'. The overall yield of 1' from 2 is thus 27%. As previously described, 2 is readily available in optically homogeneous form from cis-1,4 diacetoxycyclopentene.

Scheme VI

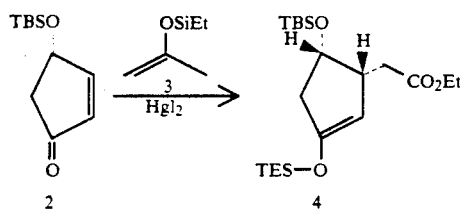

-continued
Scheme VI

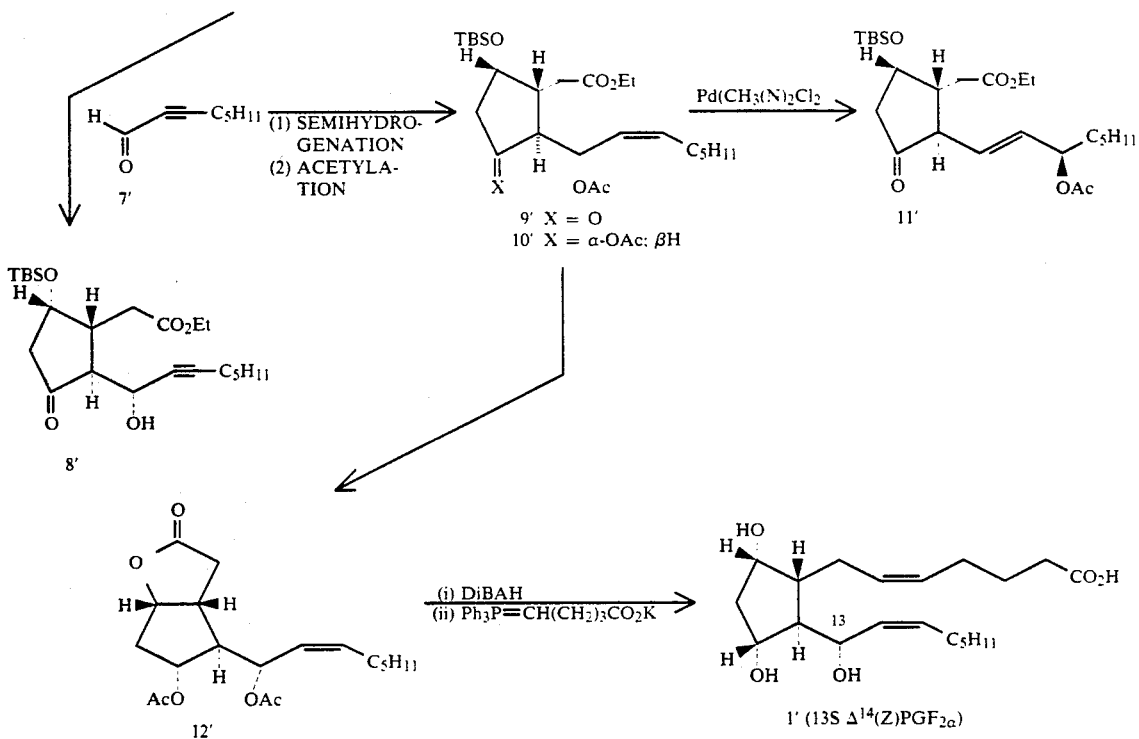

The stereochemical outcome at $C_{13}$ arising from the coupling of similar substrates under the same conditions is surprising. In the previously described aldols (Danishefsky, S. J., Cabal, M. P., Chow, K., J. Am. Chem. Soc., 111, 3456 (1989)) leading to 7 to 8 no other stereoisomers were observed. Yet when the ynal 7' is employed 8' was the only product observed!

We respect to the "Z-enal process" described hereinabove the following is a non-limiting summary of process variations for each step:
(a) other possible solvent(s): tetrahydrofuran temperature range: ±5° C.
time range: At 0° C.: 45 minutes to 1 hour At −78° C.: 10 to 15 minutes
Mole ratio of reactants (relative to cyclopentenone):
Lewis acid, e.g., $HgI_2$ - 5-10 mole %
Ketene acetal - 300 to 500 mole %
(b) other possible solvent(s): 1,2-dichloroethane temperature range: −85° to −100° C.
time range: 45 minutes to 1 hour
Mole ratio of reactants (relative to enol ether):
Z octenal - 200 to 300 mole % $TiCl_4$ - 100 mole %
(c) other possible solvent(s): tetrahydrofuran, ethyl ether, N,N-dimethylformamide
temperature range: =±10° C.
time range: 2 to 5 hours
Mole ratio of reactants (relative to aldol adduct):
Acetic Anhydride 500 - 1000 mole %
Pyridine 500 to 1000 mole %
Dimethylamino pyridine 5-10 mole %
(d) other possible solvent(s): ethyl ether
temperature range: ±5° C.
time range: 4 to 6 hours
Mole ratio of reactants (relative to product from (c)):
10 to 12 mole % of Pd $(MeCN)_2Cl_2$
(e) temperature range: 0° to 10° C.

time range: 20 to 30 minutes
mole ratio of reactants (relative to product from (d)):
$NaBH_4$ - 1000–15000 mole %
(f) same as in step (c)
(g) temperature range: 0° C.-25° C.
time range: 45 minutes to 1 hour
Mole ratio of reactants (relative to product from (f)):
TBAF - 200 to 500 mole %
(h) other possible solvent(s): methylene chloride
temperature range: ±10° C.
time range: 20-30 minutes
Mole ratio of reactants (relative to product from (g)):
DIBAH - 500-900 Mole %
(i) other possible solvent(s): ethyl ether
temperature range: ±5° C.
time range: 4 to 6 hours
Mole ratio of reactants (relative to product from (h)):
400 to 900 mole % potassium t-butoxide 200-450 mole % phosphonium salt With respect to the "E-Enal Process" described hereinabove the following is a non-limiting summary of process variations for each step:
(a) same as (a) in the "Z-Enal Process"
(b) other possible solvent(s): 1,2-dichloroethane
temperature range: ±5° C.
time range: 20 minutes to 30 minutes
mole ratio of reactants (relative to product from (a)):
E-octenal - 200 to 300 mole % $TiCl_4$ - 100 mole %
(c) no major variations
(d) same as (c) in the "Z-Enal Process"
(e) same as (d) in the "Z-Enal Process"
(f) same as (e) in the "Z-Enal Process"
(g) other solvents: tetrahydrofuran, ethyl ether
temperature range: ±5° C.
time range: 1.5 to 2 hours mole ratio of reactants (relative to product from (f)): 200 to 500 mole % of DHP 5 to 10 mole % of T$_s$OH (h) same as (g) in the "Z-Enal Process" except: time range: 5 to 6 hours (i) time range: 1 to 2 hours temperature range: ±5° C.

mole ratio of reactants (relative to product from (h)): 100 to 120 mole % of NaOMe (j) no major variations (k) same as (h) in the "Z-Enal Process"

With respect to the "13-hydroxy Prostaglandin Process" described hereinabove the following is a non-limiting summary of process variations for each step:

(a) same as (a) in "Z-Enal Process"

(b) other possible solvent(s): 1,2-dichloroethane temperature range: ±5° C. time range: 10-20 minutes mole ratio of reactants (relative to product from (a)): 200-300 mole % of Octynal 100 mole % TiCl$_4$ (c) other possible solvent(s): ethanol, methanol temperature range: ±5° C. time range: 50 minutes mole ratio of reactants (relative to product from (b)): 5 to 10wt % Lindlar's catalyst (d) same as (c) in the "Z-Enal Process"

(e) same as (e) in the "Z-Enal Process"

(f) same as (d)

(g) same as (g) in the "Z-Enal Process"

(h) same as (h) in the "Z-Enal Process"

(i) other possible solvent(s): ethyl ether temperature range: ±5° C. time range: 5-6 hours mole ratio of reactants (relative to product from (h)): 500-600 mole % of ylid (13')

Prostaglandins are known to have various pharmacological effects such as vasodilation, inhibition of platelet aggregation, and stimulation of intestinal and uterine smooth muscles. Prostaglandins have also been used as hypotensives and abortifacients.

The invention will now be described with reference to the following non-limiting examples.

EXAMPLES

EXAMPLES 1

(−)-[3R-(3α,4α)]-(1-Triethylsilyloxy-4-t-butyldimethylsilyloxycyclopentenyl)ethylacetate (4)

To a solution of cyclopentenone 2 (3.00 g, 14.1 mmol) in anhydrous Et$_2$O (120 ml) was added HgI$_2$ (300 mg, 0.66 mmol) under nitrogen. After stirring at room temperature for one hour, the mixture was cooled to −78° C. and a solution of the silylketene acetal 3 (11.17 g, 56.5 mmol) in Et$_2$O (10 ml) was added over 5 minutes. After 10 minutes Et$_3$N (3 ml) was added and the cold bath removed. The solution was allowed to warm to room temperature and then filtered through a SiO$_2$ column (10:1 hexanes/ethyl acetate) deactivated with Et$_3$N (5%). The solvent was evaporated and the residue was rechromatographed (9:1 hexanes/ether) to give 5.40 g of silylenolether 4 (92%); $^1$H NMR (250 MHz, CDCl$_3$)δ 4.57 (br. s, 1H, HC-OTBS), 4.47 (app. dd, 1H, J=13.7 Hz, vinyl), 4.11 (2q, 2H, —OCH$_2$—Me), 3.05 (app. dd, 1H, J=13.3, 8.5 Hz, CH allylic), 2.59 (dd, 1H, J=15.9, 6.7 Hz, CH$_2$—CO$_2$Et), 2.42 (dd, 1H, J=15.7, 7.3 Hz, —CH$_2$ ring), 2.26 (dd, 1H, J=15.5, 6.0 Hz, —CH$_2$—r-ing), 2.19 (dd, 1H, J=15.9, 8.2 Hz, CH$_2$—CO$_2$Et), 1.27 (t, 3H, J=7.1 Hz, CH$_3$—CH$_2$O—), 0.94-1.00 (m, 9H, (CH$_3$—CH$_2$)$_3$—Si), 0.88 (s, 9H, t-Bu), 0.66-0.72 (m, 6H, (CH$_3$—CH$_2$)$_3$—Si), 0.05 and 0.03 (s each, 6H, 2-OSiCH$_3$); IR (CHCl$_3$) 2955, 1736, 1642, 1257, 1107 cm$^{-1}$; Mass Spect m/z 357 (M$^-$—C$_4$H$_9$2), 415 (M$^+$+1); [α]$_D$-11.60° (c=1.1, CHCl$_3$)

EXAMPLE 2

(−)-[3R-(2β(2Z.1R*),3α,4α)]-[2-(1-acetoxy-2-octenyl)-4-t-butyldimethylsilyloxy-1-oxocyclopenty]-ethylacetate (7)

TiCl$_4$ (1.32 ml, 12.0 mmol) was added rapidly via syringe to a solution of silylenolether 4 (5.00 g, 12.0 mmol) and Z-octenal (3.00 g, 24.0 mmol) in anhydrous Cl$_2$CH$_2$ (180 ml) at −85° C. After 45 minutes the reaction was quenched by the addition of H$_2$O (20 ml) and the resulting mixture was allowed to warm to room temperature. The layers were separated and the aqueous layer was further extracted with ethyl acetate. The combined organic layers were dried over MgSO$_4$, evaporated and concentrated. The residue was dissolved in Cl$_2$CH$_2$ (100 ml). Pyridine (9.70 ml, 120 mmol) and Ac$_2$O (11.3 ml, 120 mmol) were added to this solution using catalytic DMAP (20 mg). After stirring at room temperature for 2.5 hours the mixture was concentrated and the residue was chromatographed (5:1, hexane/ethyl acetate) to afford 2.70 g of the aldol product 7 (50%); $^1$H-NMR (250 MHz, CDCl$_3$) δ 5.84 (dd, 1H, J=8.9, 3.1 Hz, CH-OAc), 5.57 (dt, 1H, J=10.8, 7.3 Hz, =CH—CH$_2$ vinyl), 5.30 (dd, 1H, J=10.8, 9.2 Hz, =CH—CHOAc vinyl), 4.56 (br s, 1H, J=0.5 Hz, CH=OTBS), 4.16 (q, 2H, J=14.2, 7.1 Hz, —O—CH$_2$Me), 2.60-2.80 (m, 3H, —CH—CH$_2$CO$_2$Et), 2.32 (d, 2H, J=2.5 Hz, —CH$_2$— in ring), 2.03-2.29 (m, 3H, —CH—C(O)— in ring and CH$_2$ allylic), 2.00 (s, 3H, CH$_3$—CO$_2$—), 1.26-1.32 (m, 9H, 3CH$_2$ in chain and methyl group in ester), 0.84-0.91 (m, 3H, CH$_3$-terminal chain), 0.85 (s, 9H, t-butyl), 0.03 and 0.01 (s each, 6H, 2-OSiCH$_3$); IR (CHCl$_3$) 2928, 1753, 1733, 1232 cm$^{-1}$; [α]$_D$ −8.2° (c=1.1, CHCl$_3$); Mass Spect m/z 411 (M$^+$—C$_4$H$_9$); HRMS calcd. (M$^+$+H) 469.2986, found 469.2966. Anal. Calcd. for C$_{25}$H$_{44}$SiO$_6$:C, 64.06; H, 9.46. Found: C, 63.99; H, 9.48.

EXAMPLE 3

(−)-[3R-2β(2E,1R*),3α,4α)]-[1-acetoxy-2-octenyl)-4-t-butyldimethylsilyloxy-1-oxocyclopentyl]-ethylacetate (8)

0.50 g (1.21 mmol) of (−)-[3R-(3α,4α)]-(1-triethyl-silyloxy-4-t-butyl-dimethylsilyloxy cyclopentenyl) ethylacetate 4 and 0.30 g (2.42 mmol) of 2-trans-octenal were added to 20 mL of dry CH$_2$Cl$_2$ under nitrogen. The solution was cooled to −78° C. prior to addition of 0.13 mL (1.21 mmol) of TiCl$_4$. After stirring at −78° C. for 0.5 hours the reaction was quenched with water. The reaction mixture was washed with water (3×) followed by brine. The organic phase was dried over MgSO$_4$, filtered and concentrated. The residue was dissolved in 15 mL of a HOAc/H$_2$O/THF (10:3.3:1) solution. After stirring at room temperature for 5 hours the reaction mixture was washed with 5% NaHCO$_3$ (3×) followed by water and brine. The organic phase was dried over MgSO$_4$, filtered and concentrated. The residue was dissolved in 20 mL of CH$_2$Cl$_2$ followed by addition of 0.98 mL (12.1 mmol) of pyridine, 1.14 mL (12.1 mmol) of acetic anhydride, and a catalytic amount of DMAP. After stirring at room temperature for 11 hours the reaction mixture was washed with water (3×) followed by brine. The organic phase was dried over MgSO$_4$, filtered and concentrated. The residue was subjected to SiO$_2$ chromatography (6:1 hexanes/ethyl acetate) to afford 0.33 g (0.71 mmol, 59%) of 8. $^1$H MNR (250 MHz, CDCl$_3$) δ 5.68 (dt, J=14.8, 7.1 Hz, =CHCH$_2$, 1H), 5.54 (dd, J=6.8, 2.8 Hz, —CH(OAc), 1H), 5.37 (dd, J=15.4, 6.7 Hz, =CHCH(OAc), 1H) 4.55 (d, J=2.3 Hz, —CH(OTBS), 1H), 4.14 (q, J=7.1 Hz, —CO$_2$CH$_2$, 2H), 2.58-2.75 (m, 3H), 2.23-2.30 (m, 1H), 2.29 (d, J=2.8 Hz, —CH$_2$C(O), 2H), 1.98-2.06 (m, 2H), 2.02 (s, —C(O)CH$_3$, 3H), 1.16-1.40 (m, 6H), 1.27 (t, J=7.1 Hz, —CO$_2$CH$_2$CH$_3$, 3H), 0.83-0.89 (m, 3H), 0.84 (s, —OSi(C$_4$H$_9$), 9H), 0.02 (s, —OSiCH$_3$, 3H), 0.00 (s, —OSiCH$_3$, 3H); IR (film) 2920, 2850, 1750, 1730, 1230 cm$^{-1}$; Mass Spect. m/z 411(M$^+$-C$_4$H$_9$); HRMS calcd. (M$^+$+H) 469.2986, found 469.2967; anal. calcd. for C$_{25}$H$_{44}$O$_6$Si: C, 64.10; H, 9.40, found C, 64.05; H, 9.31; [α]$_D$ −34° (c=0.47, CHCl$_3$).

EXAMPLE 4

(+)-[3R-(2β(1E,3S*),3α,4α)]-[2-(3-acetoxy-1-octenyl)-4-t-butyldimethylsilyloxy-1-oxocyclopenty]-ethylacetate (9)

PdCl$_2$(CH$_3$CN)$_2$ (29.3 mg, 0.11 mmol) was added under nitrogen to a solution of aldol product 7 (530 mg, 1.13 mmol) in anhydrous THF (40 ml) at room temperature. After 4 hours the solvent was evaporated and the residue was flash chromatographed (5:1, hexanes/ethyl acetate) to afford 380 mg of 9 (72%) as a yellow oil; $^1$H-NMR (250 MHz, CDCl$_3$) δ 5.58 (dd, 1H, J=15.5, 5.5 Hz, =CH—CH(OAc)), 5.48 (dd, 1H, J=15.5, 6.9 Hz, =CH—CH—ring), 5.24 (dd, 1H, J=12.3, 5.6 Hz, CH(OAc)), 4.58 (br t, 1H, J=3.3 Hz, CH—OTBS), 4.14 (q, 2H, J=14.3, 7.1 Hz, OCH$_2$—Me), 2.59-2.78 (m, 2H, CH$_2$—CO$_2$Et), 2.30-2.49 (m, 4H, —CH$_2$— and two —CH— in ring), 2.05 (s, 3H, CH$_3$—CO$_2$—), 1.57-1.65 (m, 2H, CH$_2$—Bu in chain), 1.25-1.30 (m, 9H, 3 —CH$_2$— in chain and methyl group in ester), 0.86-0.90 (m, 3H, CH$_3$-terminal chain), 0.86 (s, 9H, t-butyl), 0.03 and 0.02 (s each, 6H, two —OSiCH$_3$); IR (CHCl$_3$) 2934, 1738, 1243 cm$^{-1}$; [α]$_D$ +8.3° (c=1.0, CHCl$_3$); Mass Spect. m/z 411 (M$^+$—C$_4$H$_9$); HRMS, calcd. C$_{25}$H$_{44}$SiO$_6$(M$^+$—C$_4$H$_9$) 411.2203, found 411.2216.

EXAMPLE 5

(+)-[1R-[1α,2β(1E,3S*),3α,4α]]-[1-acetoxy-2-(3-acetoxy-1-octenyl)-4-(t-butyldimethylsilyloxy)cyclopenty]-ethylacetate (11)

NaBH$_4$ (460 mg, 12.00 mmol) was added under nitrogen to a solution of (+)-[3R-(2β(1E, 3S*), 3α,4α)]-[2-(3-acetoxy-1-octenyl)-4-t-butyldimethylsilyloxy-1-oxocyclopentyl]-ethylacetate 9 (380 mg, 0.81 mmol) in anhydrous MeOH (20 ml) at 0° C. After 20 minutes, the reaction was quenched by the addition of H$_2$O (3 ml). The mixture was extracted with ethyl acetate (5×5 ml) and dried over MgSO$_4$. Solvents were evaporated and the residue was redissolved in Cl$_2$CH$_2$(30 ml). Catalytic DMAP (20 mg), pyridine (655 ml, 8.10 mmol) followed by Ac$_2$O (763 ml, 8.10 mmol) were added. After 2 hours at room temperature, the mixture was concentrated and the crude was purified by SiO$_2$ chromatography (5:1, hexanes/ethyl acetate) to give 307 mg of diacetate 11 (74%); $^1$H-NMR (250 MHz, CDCl$_3$) δ 5.48-5.52 (m, 2H, vinyl), 5.21 (dd, 1H, J=5.2, 3.5 Hz, CH—(OAc)-chain), 4.82-4.90 (m, 1H, CH(OAc)ring), 4.28 (br t, 1H, J=4.4 Hz, CH—OTBS), 4.11 (q, 2H, J=14.3, 7.2 Hz, —OCH$_2$—Me), 2.21-2.60 (m, 4H), 1.98-2.10 (m, 1H), 2.05 (s, 3H, CH$_3$—CO$_2$—chain), 2.01 (s, 3H, CH$_3$—CO$_2$—ring), 1.46-1.62 (m, 3H), 1.23-1.30 (m, 9H, 3 CH$_2$ in chain and methyl group in ester), 0.85-0.91 (m, 3H, CH$_3$-terminal chain), 0.89 (s, 9H, t-butyl), 0.02 and 0.01 (s each, 6H, two —OSiCH$_3$); IR (CHCl$_3$) 2934, 1740, 1240 cm$^{-1}$; [α]$_D$ +24.8° (c=1.17, CHCl$_3$); Mass Spect. m/z 455 (M$^-$ —C$_4$H$_9$); HRMS calcd. (M$^-$+H) 513.3249, found 513.3242. Anal. Calcd. for C$_{27}$H$_{48}$SiO$_7$; C, 63.24; H, 9.43. Found: C, 63.33; H. 9.29.

EXAMPLE 6

(−)-[3aα,4β(1E,3S*),5α,6aα]-[5-acetoxy-4-(3-acetoxy-1-octenyl)]perhydrocyclopenta[b]furan-2-one (12)

Bu$_4$NF (2.58 ml, 1M solution in THF, 2.58 mmol), was added under nitrogen to a solution of diacetate (+)-[1R-[1α,2β(1E,3S*),3α,4α]]-[1-acetoxy-2-(3-acetoxy-1-octenyl)-4-(t-butyldimethylsilyloxy)cyclopentyl]-ethylacetate 11 (441 mg, 0.86 mmol) in anhydrous THF (40 ml) at 0° C. The cold bath was removed when the addition was finished. After 45 minutes the mixture was concentrated and the crude was chromatographed (2:1, hexanes/ethyl acetate) to afford 272 mg of lactone 12 (90%); $^1$H-NMR (250 MHz, CDCl$_3$) δ 5.49-5.52 (m, 2H, vinyl), 5.18 (br dd, 1H, J=10,6 Hz, —CH(OAc) chain), 4.94-5.04 (m, 2H, —CH(OAc) ring and —CH—O(CO)ring), 2.77-2.92 (m, 2H), 2.59-2.69 (br dd, 1H), 2.37-2.50 (m, 2H), 2.14 (br d, 1H), 2.05 (s, 3H, CH$_3$—CO$_2$-chain), 2.03 (s, 3H, CH$_3$—CO$_2$— ring), 1.54-1.62 (m, 2H), 1.28 (br s, 6H, 3 —CH$_2$— in chain), 0.86-0.95 (m, 3H, CH$_3$-terminal chain); IR (CHCl$_3$) 2929, 1775, 1739, 1240 cm$^{-1}$; [α]$_D$−37.1° (c=1.24, CHCl$_3$); Mass Spect. m/z 294.23 (M$^+$—C$_4$H$_9$) Anal. Calcd. for C$_{19}$H$_{28}$O$_6$:C, 64.75; H, 8.00. Found: C, 64.31; H, 7.94.

EXAMPLE 7

[3aα,4β(1E,3S*),5α,6aα]-[2,5-dihydroxy-4-(3-hydroxy-1-octenyl)]hexahydro-2H-cyclopenta[b]furan (13)

Diisobutyl-aluminium hydride (6.12 mL, 1M solution in hexane, 6.12 mmol) was added under nitrogen to a solution of lactone 12 (−)-[3aα,4β(1E,3S*),5α,6aα]-[5-acetoxty-4-(3-acetoxy-1-octenyl)]perhydrocyclopenta[b]furan-2-one (240 mg, 0.68 mmol) in anhydrous toluene (40 mL) at −78° C. After 20 minutes the reaction was quenched by the addition of MeOH (1 mL) at −78° C. The cold bath was removed and the reaction mixture was allowed to warm to room temperature. The solution was diluted with Et$_2$O (15 mL) and potassium sodium tartrate (Rochelle's salt) was added and the mixture was stirred until the two phases were clear. The layers were separated and the aqueous layer was further extracted with ethyl acetate and dried over MgSO$_4$. Purification of the crude product by SiO$_2$ chromatography (9:1, CHCl$_3$/MeOH) afforded 145 mg of 7 (79%); $^1$H-NMR (250 MHz, CDCl$_3$) δ 5.61 (br dd, 1H, —CHOH— furan ring), 5.37-5.59 (m, 2H, vinyl), 4.54 (ddd, 1H, J=13.6, 6.8, 2.5 Hz, —CHO-furan ring), 3.97-4.04 (m, 1H, CHOH chain) 3.78-3.88 (m, 1H, CHOH-ring), 2.67-2.74 (m, 1H), 2.31-2.45 (m, 2H), 2.10-2.30 (m, 1H), 1.94-2.07 (m, 2H), 1.19-1.90 (m, 2H), 1.28 (br s, 6H, 3 —CH$_2$— in chain), 0.88 (t, 3H, J=6.4 Hz, CH$_3$-terminal chain); IR (CHCl$_3$) 3365, 2929, 960 cm$^{-1}$; Mass Spect. m/z 252.17 (M$^+$—H$_2$O).

EXAMPLE 8

(+)-[3R-(2β(1E,3R*),3α,4α)]-[2-(3-acetoxy-1-octenyl)-4-t-butyldimethylsiloxy-1-oxocyclopentyl]ethylacetate (15)

0.33 g (0.71 mmol) of 8 (−)-[3R-2β(2E,1R*),3α,4α)]-[1-acetoxy-2-octenyl)-4-t-butyldimethylsilyloxy-1-oxocylopentyl]ethylacetate and 18.4 mg (0.071 mmol) of bis(acetonitrile)palladium(II) chloride were added to 71 mL of THF. After stirring at room temperature for 2 hours the reaction mixture was concentrated and the residue subjected to $SiO_2$ chromatography (6:1 hexanes/ethyl acetate) to afford 0.28 g (0.60 mmol, 85%) of 15. $^1$H NMR (250 MHz, CDCl$_3$) δ 5.54 (dd, J=15.5, 6.4 Hz, =CHC(OAc), 1H), 5.43 (dd, J=15.5, 7.2 Hz, =CHCH, 1H), 5.20 (dt (app.q), J=6.4 Hz, —CH(OAc), 1H), 4.57 (t, J=3.5 Hz, —CH(OTBS), 1H), 4.13 (q, J=7.2 Hz, —CO$_2$CH$_2$, 2H), 2.57–2.75 (m, 2H), 2.28–2.48 (m 4H), 2.02 (s, —C(O)CH$_3$, 3H), 1.53–1.61 (m, 2H), 1.23–1.28 (m, 6H), 1.26 (t, J=7.2 Hz, —CO$_2$CH$_2$CH$_3$, 3H), 0.84–0.89 (m, 3H), 0.84 (s, —OSi(C$_4$H$_9$), 9H), 0.02 (s, —OSiCHhd 3, 3H), 0.00 (s, —OSiCH$_3$, 3H); IR (film) 2920, 2850, 1735, 1240 cm$^{-1}$; Mass Spect. m/z 411 (M$^+$—C$_4$H$_9$); HRMS Calcd. (M$^+$+H) C$_{25}$H$_{44}$O$_6$Si: 469.2985, found 469.2953; [α]$_D$ +51° (c=1.17, CHCl$_3$).

EXAMPLE 9

(+)-[1R-[1α,2β(1E,3R*),3α,4α)]]-[2-(3-acetoxy-1-octenyl)-1-hydroxy-4-(t-butyldimethylsiloxy)cyclopentyl]-ethylacetate (16)

0.28 g (0.60 mmol) of 15 (+)-[3R-(2β(1E,3R*),3α,4α)]-[2-(3-acetoxy-1-octenyl)-4-t-butyldimethylsiloxy-1-oxocyclopentyl]ethylacetate was added to 25 mL of methanol and the solution cool to 0° C. 0.34 g (9.0 mmol) of sodium borohydride was added. After stirring at 0° for 0.5 hours the reaction was quenched with water and the mixture extracted with ethyl acetate. The organic phase was dried over MgSO$_4$, filtered and concentrated. The residue was subjected to $SiO_2$ chromatography (6:1 hexanes/ethyl acetate) to afford 0.24 g (0.51 mmol, 85%) of 16. $^1$H NMR (250 MHz, CDCl$_3$) δ 5.48–5.51 (m, HC=CHCH(OAc), 2H), 5.16–5.24 (m, —CH(OAc), 1H), 4.32 (t, J=3.7 Hz, —CH(OTBS), 1H), 4.09 (q, J=7.2 Hz, —CO$_2$CH$_2$, 2H), 3.84–3.90 (m, 1H), 2.54 (dd, J=17, 10.4 Hz, 1H), 1.91–2.33 (m, 5H), 2.03 (s, —C(O)CH$_3$, 3H), 1.49–1.75 (m, 3H), 1.21–1.30 (m, 6H), 1.24 (t, J=7.2 Hz, —CO$_2$CH$_2$CH$_3$, 3H), 0.84–0.89 (m, 3H), 0.88 (s, —OSi(C$_4$H$_9$), 9H), 0.05 (s, —OSiCH$_3$, 3H), −0.01 (s, —OSiCH$_3$, 3H); IR (film) 3460 (br), 2920, 2850, 1730, 1240 cm$^{-1}$; Mass Spect m/z 413 (M$^+$—C$_4$H$_9$); HRMS calcd. (M$^+$+H) 471.3141, found 471.3111; Anal. calcd. for C$_{25}$H$_{46}$O$_6$Si: C, 63.83; H, 9.79, found C, 63.88; H, 9.57; [α]$_D$ +57° (c=1.44, CHCl$_3$).

EXAMPLE 10

[1R-[1α,2β(1E,3R*),3α,4α)]]-[2-(3-acetoxy-1-octenyl-1-tetrahydropyranyl-4-(t-butyldimethylsiloxy)cyclopentyl]ethylacetate (17)

0.24 g (0.51 mmol) of 16 (+)-[1R-[1α,2β(1E,3R*),3α,4α)]]-[2-(3-acetoxy-1-octenyl)-1-hydroxy-4-(t-butyldimethylsiloxy)cyclopentyl]-ethylacetate, 0.23 ml (2.55 mmol) of DHP, and a catalytic amount of TsOH were added to 30 mL of CH$_2$Cl$_2$. After 1.5 hours of stirring at room temperature the reaction was quenched with saturated NaHCO$_3$. The mixture was washed with water (2 times) followed by brine. The organic phase was dried over MgSO$_4$, filtered and concentrated. The residue was subjected to $SiO_2$ chromatography (9:1 hexanes/ethyl acetate) to afford 0.27 g (0.49 mmol, 96%) of 17. $^1$H NMR (250 MHz, CDCl$_3$) mixture of diastereomers; IR (film) 2920, 2850, 1730, 1240 cm$^{-1}$; Mass Spect m/z 497 (M$^-$—C$_4$H$_9$); HRMS calcd. (M$^+$+H) 555.3716, found 555.3697; Anal. calcd. for C$_{30}$H$_{54}$O$_7$Si: C, 64.98; H, 9.75, found C, 64.77; H, 9.83; [α]$_D$ +54° (c=1.33, CHCl$_3$).

EXAMPLE 11

[3aα,4β(1E,3R*),5α,6aα]-[5-tetrahydropyranyl-4-(3-acetoxy-1-octenyl)]perhydrocyclopenta[b]furan-2-one (18)

0.27 g (0.49 mmol) of 17 [1R-[1α,2β(1E,3R*),3α,4α)]]-[2-(3-acetoxy-1-octenyl-1-tetrahydropyranyl-4-(t-butyldimethylsiloxy)cyclo-pentyl]ethylacetate and 2.43 mL (2.45 mmol) of a 1M solution of TBAF were added to 20 mL to THF. After stirring at room temperature for 5.5 hours the reaction mixture was diluted with water. The mixture was extracted with ethyl acetate (3 times). The organic phase was dried over MgSO$_4$, filtered and concentrated. The residue was subjected to $SiO_2$ chromatography (2:1 hexanes/ethyl acetate) to afford 0.16 g (0.41 mmol, 84%) of 18. $^1$H NMR (250 MHz, CDCl$_3$) mixture of diastereomers; IR (film) 2930, 2855, 1770, 1730, 1240 cm$^{-1}$; Mass Spect m/z 250 (M$^+$-(C$_5$H$_9$O+CO$_2$CH$_3$)); HRMS calcd. (M$^-$+H) 395.2433, found 395.2437; Anal. calcd. for C$_{22}$H$_{34}$O$_6$: C, 67.01; H, 8.63, found C, 67.08; H, 8.53; [α]$_D$ +17° (c=1.03, CHCl$_3$).

EXAMPLE 12

[3aα,4β(1E,3R*),5α,6aα]-[5-tetrahydropyranyl-4-(3-hydroxy-1-octenyl)]perhydrocyclopenta[b]furan-2-one (19)

0.16 g (0.41 mmol) of 18 [3aα,4β(1E,3R*),5α,6aα]-[5-tetrahydropyranyl-4-(3-acetoxy-1-octenyl)]perhydrocyclopenta[b]furan-2-one was added to 5 mL of methanol. Added to the solution was 0.10 mL (0.45 mmol) of a 4.37M NaOMe solution. After stirring at room temperature for 2 hours the reaction was quenched with saturated NH$_4$Cl. The reaction mixture was extracted with ethyl acetate (3 times). The organic phase was dried over MgSO$_4$, filtered and concentrated. The residue was subjected to $SiO_2$ chromatography (3:1 ethyl acetate/hexanes) to afford 0.14 g (0.40 mmol, 98%) of 19. $^1$H NMR (250 MHz, CDCl$_3$) mixture of diastereomers; IR (film) 3440 (br), 2930, 2850, 1765 cm$^{-1}$; Mass Spect m/z 250 (M$^+$-(C$_4$H$_9$+OH); HRMS calcd. (M$^+$+H) 353.2327, found 353.2306; Anal. calcd. for C$_{20}$H$_{32}$O$_5$: C, 68.18; H, 9.09, found C, 68.31; H, 9.11; [α]$_D$ −22° (c=0.75, CHCl$_3$).

EXAMPLE 13

[3aα,4β(1E,3S*),5α,6aα]-[5-tetrahydropyranyl-4-(3-benzoyloxy-1-octenyl)perhydrocyclopental[b]furan-2-one (20)

0.14 g (0.40 mmol) of 19 [3aα,4β(1E,3R*),5α,6aα]-[5-tetrahydropyranyl-4-(3-hydroxy-1-octenyl)]perhydrocyclopenta[b]furan-2-one, 0.21 g (0.80 mmol) of triphenylphosphine, 98 mg (0.80 mmol) of benzoic acid, and 0.13 mL (0.80 mmol) of DEAD were added to 20 mL of THF. After stirring at room temperature for 5 minutes the reaction was quenched with saturated NaHCO$_3$. The reaction mixture was diluted with water and extracted with ether (3 times). The organic phase was dried over $MgSO_4$, filtered and concentrated. The residue was subjected to $SiO_2$ chromatography (2:1 hexanes/ethyl acetate) to afford 0.13 g (0.29 mmol, 73%) of 20. $^1$H NMR (250 MHz, $CDCl_3$) mixture of diastereomers; IR (film) 2920, 2850, 1770, 1615, 1270 $cm^{-1}$; Anal. calcd for $C_{27}H_{36}O_6$ : C, 71.05; H, 7.89, found C, 71.02; H, 7.69; $[\alpha]_D$ −5.4° (c=1.15, $CHCl_3$).

EXAMPLE 14

[1R-[1α,2β(1E,3S*),3α,4α]]-7-[1,4-dihydroxy-2-(3-hydroxy-1-octenyl)-cyclopentyl]-5-heptenoic acid (1) (PGF$_{2\alpha}$)

The Wittig reaction was followed as described in Newton, R. F.; Reynolds, D. P.; Webb, C. F.; Young, S. N.; Grudzins, Z.; Roberts, S. M., *J. Chem. Soc. Perkin I*, 1979, 2789; Howard, C. C.; Newton, R. F.; Reynolds, D. P.; Wadsworth, A. H.; Kelly, D. R.; Roberts, S. M., *J. Chem. Soc. Perkin I*, 1980, 852 and Roberts, S. M., *J. Chem. Soc. Perkin I*, 1979, 2789. The lactol 13 [3aα,4β(-1E,3S*),5α,6aα]-[2,5-dihydroxy4-(3-hydroxy-1-octenyl)]hexahydro-2H-cyclopenta[b]furan (86.0 mg, 0.32 mmol) was dissolved in anhydrous tetrahydrofuran (4 mL) and added to a stirred mixture of potassium t-butoxide (329 mg, 2.88 mmol) and (4-carboxylbutyl)-triphenyl phosphonium bromide (638 mg, 1.44 mmol) in dry tetrahydrofuran (8 mL) at room temperature under nitrogen. The reaction mixture was stirred for 4 hours, then quenched by addition of saturated aqueous ammonium chloride (4 mL) followed by 2N hydrochloric acid (2 mL). The organic layer was separated and the aqueous layer extracted with ethyl acetate (5×5 mL). The combined extracts were washed with brine and dried over $MgSO_4$. Short-column chromatography on silica gel eluting with acetic acid-light petroleum-ethyl acetate (5:60:35) gave 60 mg of (+) PGF$_{2\alpha}$ 1 (53%). The synthetic product was spectroscopically (IR, $^1$H−NMR) and chromatographically (T.L.C.) identical with commercial product. The rotation of 1, $[\alpha]_D$ +23.5 (c=1.00, THF).

EXAMPLE 15

[3R-(2α(2Z, 1S*), 3α, 4α)]-[2-1-acetoxy-2-octenyl)-4-t-butyldimethylsilyloxy-1-oxo-cyclopentyl]-ethylacetate (9')

0.25 mL of $TiCl_4$ (2.27 mmol) was added via syringe to 0.56 g (4.54 mmol) of 2-octynal in 25 mL of dry $CH_2Cl_2$ at −78° C. After 15 minutes, 0.94 g (2.27 mmol) of silylenol ether 4 in 25 mL of dry $CH_2Cl_2$ was added over a 10 minute period. The reaction was stirred at −78° C. for 20 minutes before being quenched with water. The reaction mixture was washed with water (2 times) followed by brine. The organic phase was dried over $MgSO_4$, filtered and concentrated. The residue was subjected to $SiO_2$ chromatography (9:1 hexanes/ethyl acetate) to afford 0.68 g (1.60 mmol, 70%) of the aldol adduct. The product was immediately taken on to the next step. 0.68 g (1.60 mmol) of the aldol adduct and 68 mg of Lindlar's catalyst was added to 30 mL of ethyl acetate. The mixture was evacuated and flushed with hydrogen (2 times) before it was left to stir under a hydrogen atmosphere (1 atmosphere). After 50 minutes, the reaction mixture was filtered through celite and then concentrated. The residue was dissolved in 25 mL of $CH_2Cl_2$. 1.51 mL (16.0 mmol) of acetic anhydride, 1.29 mL (16.0 mmol) of pyridine, and a catalytic amount of DMAP were added. The reaction was stirred at room temperature for overnight before being washed with water (2 times) followed by brine. The organic phase was dried over $MgSO_4$, filtered and concentrated. The residue was subjected to $SiO_2$ chromatography (6:1 hexanes/ethyl acetate) to afford 0.56 g (1.20 mmol, 75%) of 9'. Overall yield of 9' based on 4 is 53%. $^1$H NMR (250 MHz, $CDCl_3$) δ 5.85-5.90 (m, —CH(OAc), 1H), 5.57-5.66 (m, vinyl protons, 2H), 4.54-4.56 (m, —CH(OTBS), 1H), 4.17 (q, J=7 Hz, —$CO_2CH_2$, 2H), 2.56-2.78 (m, 3H), 2.03-2.40 (m, 5H), 2.03 (s, —C(O)$CH_3$, 3H), 1.29 (t, J=7 Hz, —$CO_2CH_2CH_3$, 3H), 1.26-1.40 (m, 6H), 0.89 (t, J=6 Hz, —$CH_2CH_3$, 3H), 0.85 (s, —OSiC($CH_3$)$_3$, 9H), 0.03 (s, —OSi$CH_3$, 3H), 0.01 (s, —OSi$CH_3$, 3H); IR (film) 2960, 2940, 2860, 1750, 1470, 1370, 1240 $cm^{-1}$; Mass Spect m/z 411 (M$^+$—$C_4H_9$); HRMS calcd. (M$^+$+H) 469.2985, found 469.2976; Anal. calcd. for $C_{25}H_{44}O_6Si$ : C, 64.10; H, 9.40, found C, 64.39; H, 9.43.

EXAMPLE 16

[1R-[1α,2β(2Z,1S*),3α,4α]]-[1-acetoxy-2-(1-acetoxy-2-octenyl)-4-(t-butyldimethylsilyloxy)cyclopentyl]ethylacetate (10')

0.73 g (19.2 mmol) of $NaBH_4$ was added to 0.60 g (1.28 mmol) of 9' [3R-(2α(2Z, 1S*), 3α, 4α)]-[2-1-acetoxy2-octenyl)-4-5-butyldimethyl silyloxy-1-oxo-cyclopentyl]-ethylacetate in 30 mL of MeOH at 0° C. After 20 minutes, the reaction mixture was diluted with water and extracted with ethyl acetate (4 times). The ethyl acetate phases were combined and dried over $MgSO_4$, filtered and concentrated. The residue is dissolved in 30 mL of $CH_2Cl_2$. 1.03 mL (12.8 mmol) of pyridine, 1.21 mL (12.8 mmol) of $Ac_2O$, and a catalytic amount of DMAP were added. The reaction was stirred at room temperature for 12 hours before being washed with water (3 times) followed by brine. The organic phase was dried over $MgSO_4$, filtered and concentrated. The residue was subjected to $SiO_2$ chromatography (9:1 hexanes/ethyl acetate) to afford 0.52 g (1.02 mmol, 79%) of 10'. $^1$H NMR (250 MHz, $CDCl_3$) δ 5.66 (dd, J=9,4 Hz, —CH(oAc)(CH═CH), 1H), 5.55 (dt, J=11,7 Hz, ═CH$CH_2$, 1H), 5.31 (dd, J=11, 9 Hz, ═CHC(OAc), 1H), 5.16 (ddd, J=7.7, 5.3, 2 Hz, —CH(OAc), 1H), 4.28 (ddd (app. t), J=3.3 Hz, —CH(OTBS), 1H), 4.12 (q, J=7 Hz, —$CO_2CH_2$, 2H), 2.63 (dd, J=17,9.5 Hz, 1H), 2.50 (dd, J=17,4.4 Hz, 1H), 1.95-2.25 (m, 6H), 2.02 (s, —C(O)$CH_3$, 3H), 2.00 (s, —C(O)$CH_3$, 3H), 1.23-1.69 (m, 6H), 1.26 (t, J=7 Hz, —$CO_2CH_2CH_3$, 3H), 0.88-0.91 (m, 12H), 0.01 (s, —OSi$CH_3$), 3H), IR (film) 2960, 2940, 2860, 1740, 1470, 1375, 1240 $cm^{-1}$; Mass Spect m/z 395 (M$^+$-(HOAc+$C_4H_9$)); HRMS calcd. (M$^+$+H) 513.3247, found 513.3226; Anal. calcd. for $C_{27}H_{48}O_7Si$ : C, 63.28; H, 9.38, found C, 63.41; H, 9.43.

EXAMPLE 17

[3R-(2β(1E,3R*),3α,4α)]-[1-(3-acetoxy-1-octenyl)-4-5-butyldimethylsiloxy-1-oxocyclopenty]-ethylacetate (11')

80.0 mg (0.17 mmol) of 9' [3R-(2α(2Z, 1S*), 3α, 4α)]-[2-1-acetoxy-2-octenyl)-4-t-butyldimethylsilyloxy-1-oxo-cyclopentyl]ethylacetate and 4.4 mg (0.017 mmol) of $PdCl_2(CH_3CN)_2$ were added to 17 mL of THF. The reaction was stirred at room temperature for 4 hours before it was concentrated and subjected to $SiO_2$ chromatography (5:1 hexanes/ethyl acetate) to afford 60.0 mg (0.13 mmol, 76%) of 11'. $^1$H NMR (250 MHz, CDCl$_3$) δ 5.54 (dd, J=15.5, 6.4 Hz, =CHC(OAc), 1H), 5.43 (dd, J=15.5, 7.2 Hz, =CHCH, 1H), 5.20 (dt (app.q), J=6.4 Hz, —CH(OAc), 1H), 4.57 (q, J=3.5 Hz, —CH(OTBS), 1H), 4.13 (q, J=7.2 Hz, —CO$_2$CH$_2$, 2H), 2.57-2.55 (m, 2H, 2.28-2.48 (m, 4H), 2.02 (s, —C(O)CH$_3$, 3H), 1.53-1.61 (m, 2H), 1.23-1.28 (m, 6H), 1.26 (t, J=7.2 Hz, —CO$_2$CH$_2$CH$_3$, 3H), 0.84-0.89 (m, 3H), 0.84 (s, —OSi(C$_4$H$_9$), 9H), 0.02 (s —OSiCH$_3$, 3H), 0.00 (s, —OSiCH$_3$, 3H), IR (film) 2920, 2850, 1735, 1240 cm$^{-1}$; Mass Spect. m/z 411 (M$^+$-C$_4$H$_9$); HRMS Calcd. (M$^+$+H) C$_{25}$H$_{44}$O$_6$Si : 469.2985, found 469.2953.

EXAMPLE 18

[3aα,4β(2E,1S*),5α,6aα]-[5-acetoxy-4-(3-acetoxy-1-octenyl)]perhydrocyclopenta[b]furan-2-one (12')

3.2 mL (32 mmol) of 1M TBAF solution (in THF) was added to 0.33 g (0.64 mmol) of 10' [1R-[1α,2β(2Z,1S*), 3α,4α]]-[1-acetoxy-2-(1-acetoxy-2-octenyl)-4-(t-butyldimethylsilyloxy)cyclopentyl]ethylacetate in 25 mL of THF. After 45 minutes of stirring at room temperature, the reaction mixture was diluted with water followed by extraction with ethyl acetate (3 times). The ethyl acetate phases were combined and dried over MgSO$_4$, filtered and concentrated. The residue was subjected to SiO$_2$ chromatography (3:1 hexanes/ethyl acetate) to afford 0.20 g (0.57 mmol, 89%) of 12'. $^1$H NMR (250 MHz, CDCl$_3$) δ 5.69 (dt, J=10.8, 7.6 Hz, —CHCH$_2$, 1H), 5.48 (dd (app. t), J=9.5 Hz, —CH(OAc)CH=CH, 1H), 5.27 (dd, J=10.8, 9.5 Hz, —CHC(OAc), 1H), 5.06-5.11 (m, 1H), 5.00 (t, J=6.2 Hz, 1H), 2.88 (dd, J=17.6, 10.4 Hz, 1H), 2.72-2.79 (m, 1H), 2.53 (dd, J=17.6, 1.9 Hz, 1H), 1.99-2.40 (m, 5H), 2.05 (s, —C(O)CH$_3$, 3H), 2.04 (s, —C(O)CH$_3$, 3H), 1.30-1.40 (m, 6H), 0.89 (t, J=6.4 Hz, —CH$_2$CH$_3$, 3H); IR (film) 2970, 2940, 2870, 1780, 1740, 1430, 1375, 1240 cm$^{-1}$; Mass Spect m/z 250 (M$^+$-(OAc+C(O)CH$_3$)); HRMS calcd. (M$^+$+H) 353.1964, found 353.1960.

EXAMPLE 19

[1R-[1α,2β(2Z,1S*),3α,4α]]-7-[1,4-dihydroxy-2-(1-hydroxy-2-octenyl)-cyclopentyl]-5-heptenoic acid (1')

1.45 mL (1.45 mmol) of DIBAH was added to 102.0 mg (0.29 mmol of 12' [3aα,4β(2E,1S*),5α,6aα]-[5-acetoxy-4-(3-acetoxy-1-octenyl)]perhydrocyclopenta[b]-furan-2-one in 5 mL of toluene at −78° C. After 20 minutes, 5 mL of methanol was added. The solution was diluted with ether and an equal volume of a saturated solution of Rochelle's salt. The mixture was stirred until two phases had separated out. The ether phase was dried over MgSO$_4$, filtered and concentrated. The residue was subjected to SiO$_2$ chromatography (15:1 CHCl$_3$/MeOH) to afford 76.0 mg (0.28 mmol, 97%) of the hemiacetal diol. The hemiacetal diol was immediately taken to the next step. 76.0 mg (0.28 mmol, 97%) of the hemiacetal diol in 2.5 mL of THF was added via syringe to a 5 mL solution of 13' (1.40 mmol) in THF. The reation was stirred for 5 hours at room temperature before it was quenched with saturated NH$_4$Cl. The mixture was diluted with ethyl acetate and acidified with 1 mL of 1M HCl. The ethyl acetate phase was collected and the aqueous layer extracted with ethyl acetate (2 times). The ethyl acetate phases were combined and dried over MgSO$_4$, filtered and concentrated. The residue was subjected to SiO$_2$ chromatography (8:1 CHCl$_3$/MeOH followed by 3:1 CHCl$_3$/MeOH) to afford 77.0 mg (0.22 mmol, 79%) of 1'. Overall yield of 1' from 12' is 77%. $^1$H NMR (250 MHz, CDCl$_3$) δ 5.30-5.60 (br m, vinyl protons, 4H), 4.20-4.50 (br m, 3H), 1.20-2.50 (br m, 24H), 0.92 (t, J=5 Hz, —CH$_2$CH$_3$, 3H); IR (CHCl$_3$) 3380, 2920, 1550 cm$^{-1}$; Mass Spect. m/z 351 (M$^+$-3).

Methyl Ester $^1$H NMR (250 MHz, CDCl$_3$) δ 5.38-5.65 (m, 4H, vinyl protons), 4.20-4.22 (br m, 1H), 4.09 (q, J=6.2 Hz, 1H), 3.97-4.01 (br m, 1H), 3.68 (s, —CO$_2$CH$_3$, 3H), 2.07-2.40 (m, 9H), 1.26-1.89 (m, 14H), 0.90 (t, J=6.5 Hz, —CH$_2$CH$_3$, 3H); IR (CHCl$_3$) 3495, 2952, 2932, 2855, 1723 cm$^{-1}$; Mass Spect. m/z 350 (M$^+$—H$_2$O), 332 (M$^+$—2H$_2$O).

Triacetate of Methyl Ester $^1$H NMR (250 MHz, CDCl$_3$) δ 5.73 (dd, J=9.3, 3.8 Hz, —CH(OAc)(CH=CH), 1H), 5.58 (dt, J=11.0, 7.3 Hz, —C(OAc)CH=CH, 1H), 5.31-5.43 (m, 3H), 5.21 (ddd, J=7.9, 5.2, 2.6 Hz, 1H), 5.09 (dt, J=4.7, 1.6 Hz, 1H), 3.68 (s, —CO$_2$CH$_3$, 3H), 1.20-2.36 (m, 20H), 2.06 (s, —C(O)CH$_3$, 3H), 2.04 (s, —C(O)CH$_3$, 3H), 2.03 (s, —C(O)CH$_3$, 3H), 0.90 (t, J=6.3 Hz, —CH$_2$CH$_3$, 3H).

It will be appreciated that the instant specification and claims are set forth by way of illustration and not limitation, and that various modifications and changes may be made without departing from the spirit and scope of the present invention.

What is claimed is:

1. A process for the preparation of a prosstaglandin of the formula

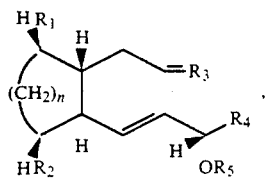

wherein n is 1, 2, 3 or 4,

R$_1$ and R$_2$, independently of each other are alkyl having 1 to 10 carbon atoms, OH, alkoxy having 1 to 10 carbon atoms, a ketone having 2 to 10 carbon atoms, a halogen, hydrogen, nitro, an amino or an ether having up to 10 carbon atoms, R$_3$ is hydrogen, alkyl having 1 to 10 carbon atoms, haloalkyl having 1 to 10 carbon atoms or carboxyalkyl having 1 to 10 carbon atoms in the alkyl moiety.

R$_4$ is hydrogen, alkyl having 1 to 10 carbon atoms or haloalkyl having 1 to 10 carbon atoms, R$_5$ is hydrogen, alkyl having 1 to 10 carbon atoms or haloalkyl having 1 to 10 carbon atoms, comprising (a) reacting an S-enone of the formula

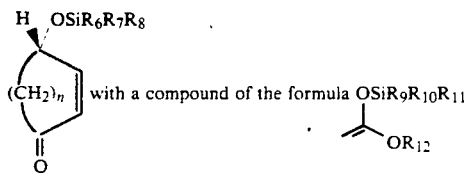

in the presence of a Lewis acid, wherein n is 1, 2, 3 or 4,

R$_6$, R$_7$ and R$_8$ combined having up to 16 carbon atoms, R$_6$, R$_7$ and R$_8$, independently of each other, are alkyl having 1 to 6 carbon atoms or wherein a combination of any two or three of $R_6$, $R_7$ and $R_8$ form an aryl having 6 to 10 carbon atoms or a cycloalkyl having 3 to 10 carbon atoms, $R_9$, $R_{10}$ and $R_{11}$ combined having up to 16 carbon atoms, $R_9$, $R_{10}$ and $R_{11}$, independently of each other are alkyl having 1 to 6 carbon atoms or wherein a combination of any two or three of $R_9$, $R_{10}$ and $R_{11}$ form an aryl having 6 to 10 carbon atoms or a cycloalkyl having 3 to 10 carbon atoms, $R_{12}$ is hydrogen or an alkyl having 1 to 10 carbon atoms, (b) reacting the compound produced from (a) with an α,β-unsaturated aldehyde of the formula

wherein $R_{13}$ is an alkyl having 1 to 10 carbon atoms or an aryl having 6 to 10 carbon atoms in the presence of $TiCl_4$, (c) acetylating the compound produced from (b),
(d) subjecting the compound produced from (c) to allylic transportation by reaction with Pd$(MeCN_2)Cl_2$,
(e) reducing the compound produced from (d),
(f) acetylating the compound produced from (e),
(g) subjecting the compound produced from (f) to a cleaving of $OSiR_6R_7R_8$ and a lactonization,
(h) subjecting the compound produced from (g) to a deacylation and
(i) reacting the compound produced from (h) with a Wittig reagent.

2. A process according to claim 1, wherein the prostaglandin is

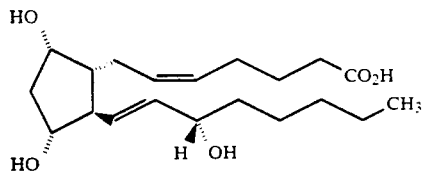

3. A process according to claim 1, wherein the S-enone is

4. A process according to claim 1, wherein the Lewis acid is $HgI_2$.

5. A process according to claim 1, wherein

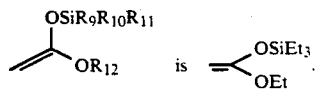

6. A process according to claim 1, wherein the α,β-unsaturated aldehyde is

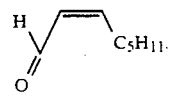

7. A process according to claim 1, wherein (c) is conducted in the presence of $AcO_2$, Py and DMAP.

8. A process according to claim 1, wherein (e) is conducted with sodium borohydride.

9. A process according to claim 1, wherein the Wittig reagent in (i) is $Ph_3P=CH-(CH_2)_3CO_2K$.

10. A process according to claim 1, wherein step (g) is conducted in the presence of TBAF.

11. A process according to claim 1, wherein step (h) is conducted in the presence of DIBAH.

12. A process for the preparation of a prostaglandin of the formula

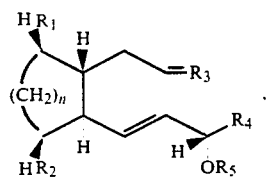

wherein n is 1, 2, 3 or 4, $R_1$ and $R_2$, independently of each other, are alkyl having 1 to 10 carbon atoms, OH, alkoxy having 1 to 10 carbon atoms, a ketone having 2 to 10 carbon atoms, a halogen, hydrogen, nitro, an amino or an ether having up to 10 carbon atoms, $R_3$ is hydrogen, alkyl having 1 to 10 carbon atoms, haloalkyl having 1 to 10 carbon atoms or carboxyalkyl having 1 to 10 carbon atoms in the alkyl moiety, $R_4$ is hydrogen, alkyl having 1 to 10 carbon atoms or haloalkyl having 1 to 10 carbon atoms, $R_5$ is hydrogen, alkyl having 1 to 10 carbon atoms or haloalkyl having 1 to 10 carbon atoms, comprising (a) reacting an S-enone of the formula

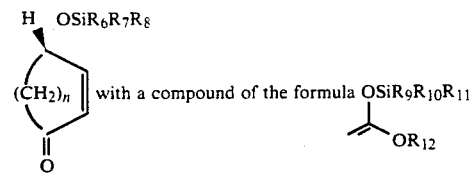

in the presence of a Lewis acid, wherein n is 1, 2, 3 or 4, $R_6$, $R_7$ and $R_8$ combined having up to 16 carbon atoms, $R_6$, $R_7$ and $R_8$, independently of each other, are alkyl having 1 to 6 carbon atoms or wherein a combination of any two or three of $R_6$, $R_7$ and $R_8$ form an aryl having 6 to 10 carbon atoms or a cycloalkyl having 3 to 10 carbon atoms, $R_9$, $R_{10}$ and $R_{11}$ combined having up to 16 carbon atoms, $R_9$, $R_{10}$ and $R_{11}$, independently of each other are alkyl having 1 to 6 carbon atoms or wherein a combination of any two or three of $R_9$, $R_{10}$ and $R_{11}$ form an aryl having 6 to 10 carbon atoms or a cycloalkyl having 3 to 10 carbon atoms, $R_{12}$ is hydrogen or an alkyl having 1 to 10 carbon atoms, (b) reacting the compound produced from (a) with an α,β-unsaturated aldehyde of the formula

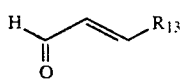

wherein $R_{13}$ is an alkyl having 1 to 10 carbon atoms or an aryl having 6 to 10 carbon atoms in the presence of $TiCl_4$,
(c) desilylating the compound produced from (b),
(d) acetylating the compound produced from (c),
(e) subjecting the compound produced from (d) to allylic transposition by reaction with Pd(MeCN$_2$)Cl$_2$,
(f) reducing the compound produced from (e),
(g) protecting the compound produced from (f) with a tetrahydropyranyl protecting group,
(h) reacting the compound produced from (g) to desilylation and lactonization,
(i) deacylating the compound produced from (h),
(j) subjecting the compound produced from (i) to a Mitsunobu reaction,
(k) deacylating the compound produced from (j),
(l) reacting the compound produced from (k) with a Wittig reagent and
(m) reacting the compound produced from (l) with a weak aqueous, organic acid, pyridinium p-toluenesulfonate or toluenesulfonic acid.

13. A process according to claim 12, wherein step (h) is conducted in the presence of TBAF.

14. A process according to claim 12 wherein step (i) is conducted in the presence of diisobutyl aluminum hydride.

15. A process according to claim 12, wherein the prostaglandin is

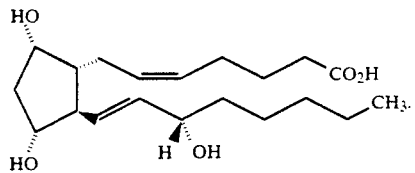

16. A process according to claim 12, wherein the S-enone is

17. A process according to claim 12, wherein the Lewis acid is $HgI_2$.

18. A process according to claim 12, wherein

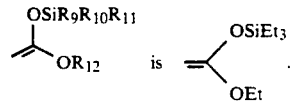

19. A process according to claim 12, wherein the α,β-unsaturated aldehyde is

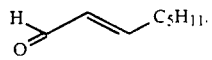

20. A process according to claim 12, wherein (f) is conducted in the presence of sodium borohydride.

21. A process according to claim 12, wherein the Mitsunobu reaction comprise a reaction in the presence of triphenylphosphine, benzoic acid and diethylazodicarboxylate.

22. A process according to claim 12, wherein the Wittig reagent is $Ph_3P=CH-(CH_2)_3CO_2Na$.

23. A process for the preparation of a prostaglandin of the formula

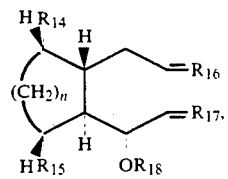

wherein n is 1, 2, 3 or 4,
$R_{14}$ and $R_{15}$, independently of each other, are alkyl having 1 to 10 carbon atoms, OH, alkoxy having 1 to 10 carbon atoms, a ketone having 2 to 10 carbon atoms, a halogen, hydrogen, nitro, an amino or an ether having up to 10 carbon atoms,
$R_{16}$ is hydrogen, alkyl having 1 to 10 carbon atoms, haloalkyl having 1 to 10 carbon atoms or carboxyalkyl having 1 to 10 carbon atoms in the alkyl moiety,
$R_{17}$ is hydrogen, alkyl having 1 to 10 carbon atoms or haloalkyl having 1 to 10 carbon atoms.
$R_{18}$ is hydrogen, alkyl having 1 to 10 carbon atoms or haloalkyl having 1 to 10 carbon atoms, comprising
(a) reacting an S-enone of the formula

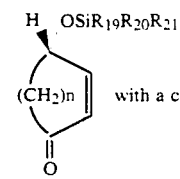

in the presence of a Lewis acid, wherein n is 1, 2, 3 or 4,
$R_{19}$, $R_{20}$ and $R_{21}$ combined having up to 16 carbon atoms, $R_{19}$, $R_{20}$ and $R_{21}$, independently of each other, are alkyl having 1 to 6 carbon atoms or wherein a combination of any two or three of $R_{19}$, $R_{20}$ and $R_{21}$ form an aryl having 6 to 10 carbon atoms or a cycloalkyl having 3 to 10 carbon atoms,
$R_{22}$, $R_{23}$ and $R_{24}$ combined having up to 16 carbon atoms, $R_{22}$, $R_{23}$ and $R_{24}$, independently of each other, are alkyl having 1 to 6 carbon atoms or wherein a combination of any two or three of $R_{22}$, $R_{23}$ and $R_{24}$ form an aryl having 6 to 10 carbon atoms or a cycloalkyl having 3 to 10 carbon atoms,
$R_{25}$ is hydrogen or an alkyl having 1 to 10 carbon atoms,
(b) reacting the compound produced from (a) with a compound of the formula

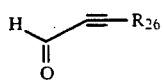

wherein $R_{26}$ is an alkyl having 1 to 10 carbon atoms in the presence of $TiCl_4$, (c) hydrogenating the compound produced from (b) with hydrogen and a hydrogenation catalyst,
(d) acetylating the compound produced from (c),
(e) reducing the compound produced from (d),
(f) acetylating the compound produced from (e),
(g) subjecting the compound produced from (f) to cleavage of $OsiR_{19}R_{20}R_{21}$ and a lactonization,
(h) reductively deacetylating the compound produced from (g), and
(i) reacting the produced from (h) with a Wittig reactant.

24. A process according to claim 23, wherein step (g) is conducted in the presence of TBAF and THF.

25. A process according to claim 23, wherein (g) is further conducted in the presence of THF.

26. A process according to claim 23, wherein the prostaglandin is

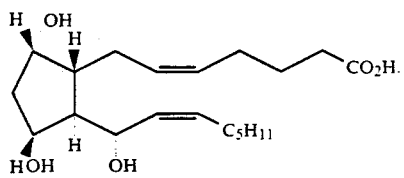

27. A process according to claim 23, wherein the S-enone is

28. A process according to claim 23, wherein the Lewis acid is $HgI_2$.

29. A process according to claim 23, wherein

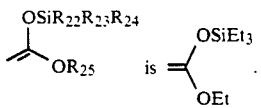

30. A process according to claim 23, wherein

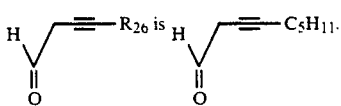

31. A process according to claim 23, wherein the hydrogenation catalyst is Lindlar's catalyst.

32. A process according to claim 23, wherein the acetylation is conducted in the presence of $Ac_2O$, Py and DMAP.

33. A process according to claim 23, wherein the reduction is conducted in the presence of sodium borohydride.

34. A process according to claim 23, wherein the reductive deacetylating is conducted in the presence of DIBAH.

35. A process according to claim 23, wherein the Wittig reagent is $Ph_3P=CH-(CH_2)_3CO_2K$.

* * * * *